(12) United States Patent
Graczyk et al.

(10) Patent No.: US 7,612,086 B2
(45) Date of Patent: Nov. 3, 2009

(54) JNK INHIBITORS

(75) Inventors: Piotr Graczyk, London (GB); Vanessa Palmer, London (GB); Afzal Khan, London (GB)

(73) Assignee: Eisai R & D Management Co. Ltd., Tokyo (JP)

( * ) Notice: Subject to any disclaimer, the term of this patent is extended or adjusted under 35 U.S.C. 154(b) by 244 days.

(21) Appl. No.: 10/554,808

(22) PCT Filed: May 14, 2004

(86) PCT No.: PCT/GB2004/002099

§ 371 (c)(1),
(2), (4) Date: Oct. 19, 2006

(87) PCT Pub. No.: WO2004/101565

PCT Pub. Date: Nov. 25, 2004

(65) Prior Publication Data

US 2007/0142366 A1 Jun. 21, 2007

(30) Foreign Application Priority Data

May 16, 2003 (GB) .................. 0311313.1
Jul. 4, 2003 (GB) .................. 0315732.8
Mar. 5, 2004 (GB) .................. 0405053.0

(51) Int. Cl.
*A61K 31/44* (2006.01)
*C07D 471/02* (2006.01)
*C07D 491/02* (2006.01)
*C07D 498/02* (2006.01)

(52) U.S. Cl. ........................ 514/300; 546/113
(58) Field of Classification Search ............ 514/300; 546/113
See application file for complete search history.

(56) References Cited

U.S. PATENT DOCUMENTS

| | | | |
|---|---|---|---|
| 4,719,218 A | 1/1988 | Bender et al. | |
| 5,439,917 A * | 8/1995 | Briving et al. | 514/300 |
| 5,714,495 A * | 2/1998 | Viaud et al. | 514/300 |
| 6,642,375 B2 | 11/2003 | Inomata et al. | |
| 7,291,630 B2 | 11/2007 | Graczyk et al. | |
| 7,314,940 B2 | 1/2008 | Graczyk et al. | |
| 2002/0013354 A1 | 1/2002 | Cheng et al. | |
| 2005/0272761 A1 | 12/2005 | Graczyk et al. | |
| 2006/0235042 A1 | 10/2006 | Graczyk et al. | |
| 2006/0270646 A1 | 11/2006 | Graczyk et al. | |
| 2007/0072896 A1 | 3/2007 | Khan et al. | |

FOREIGN PATENT DOCUMENTS

| | | |
|---|---|---|
| EP | 0 509 974 | 10/1992 |
| EP | 0 737 685 | 10/1996 |
| EP | 1 106 621 | 6/2001 |
| JP | 06 247966 A | 9/1994 |
| WO | WO-92/10498 A1 | 6/1992 |
| WO | WO-92/10499 A1 | 6/1992 |
| WO | WO-98/47899 | 10/1998 |
| WO | WO-99/20624 | 4/1999 |
| WO | WO-99/21859 | 5/1999 |
| WO | WO-99/51233 | 10/1999 |
| WO | WO-00/26210 | 5/2000 |
| WO | WO-00/26211 | 5/2000 |
| WO | WO-00/35909 | 6/2000 |
| WO | WO-00/35921 A1 | 6/2000 |
| WO | WO-00/43393 | 7/2000 |
| WO | WO-00/56710 | 9/2000 |
| WO | WO-00/64449 | 11/2000 |
| WO | WO-00/64872 | 11/2000 |
| WO | WO-01/12609 | 2/2001 |
| WO | WO-01/47922 | 7/2001 |
| WO | WO-01/49288 | 7/2001 |
| WO | WO-02/10137 | 2/2002 |
| WO | WO-02/16359 | 2/2002 |
| WO | WO-02/081475 | 10/2002 |
| WO | WO-03/028724 | 4/2003 |
| WO | WO-03/082868 | 10/2003 |
| WO | WO-03/082869 | 10/2003 |
| WO | WO-2004/016609 | 2/2004 |
| WO | WO-2004/016610 | 2/2004 |
| WO | WO-2004/078756 | 9/2004 |

OTHER PUBLICATIONS

Kontoyiannis et al., Immunity, (Mar. 1999) vol. 10, No. 3, pp. 387-398.*
Guillard et al., Heterocycles, 60(4), 2003, pp. 865-877.*
Leroy et al., Tetrahedron: Asymmetry (1997), 8(19), 3309-3318.*
U.S. Appl. No. 10/591,551.
U.S. Appl. No. 12/143,231.
Adams et al., Bioorg. Med. Chem. Lett. 2001, 11, 2867-2870.
Alam et al., Synthesis and SAR of aminopyrimidines as novel c-Jun N-terminal kinase (JNK) inhibitors:, Bioorg Med Chem Lett, vol. 17, pp. 3463-3467, 2007.
Bundgaard, Design of ProDrugs, Elsevier Science Publishers 1985.

(Continued)

*Primary Examiner*—D. Margaret Seaman
*Assistant Examiner*—Niloofar Rahmani
(74) *Attorney, Agent, or Firm*—Wilmer Cutler Pickering Hale & Dorr LLP.

(57) ABSTRACT

The present invention provides novel compounds of formula (I) and their use in the inhibition of c-Jun N-terminal kinases. The present invention further provides the use of these compounds in medicine, in particular in the prevention and/or treatment of neurodegenerative disorders related to apoptosis and/or inflammation.

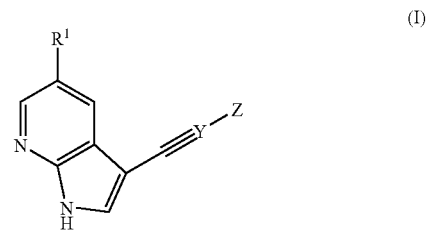

39 Claims, No Drawings

OTHER PUBLICATIONS

Cao et al., "Distinct Requirements for p38α and c-Jun N-terminal Kinase Stress-activated Protein Kinases in Different Forms of Apoptotic Neuronal Death", *The Journal of Biological Chemistry*, vol. 279, No. 34, pp. 35903-35913, Aug. 20, 2004.
CAS Accession No. 2001:432896, Registry No. 344454-31-1.
CAS Document No. 135:107148.
CAS document No. 135:43132.
Corey, E.Jr., et. al.., A synthetic Method for Formyl-Ethynyl Conversion (RCHO-RC=CH or RC=CR'), Tetrahedron Letters No. 36, Aug. 1972.
Database Beilstein, Beilstein Institute for Organic Chemistry, Citation No. 5563002 (1987).
Denmark et al., "Convergence of Mechanistic Pathways in the Palladium(0)-Catalyzed Cross-Coupling of Alkenylsilacyclobutanes and Alkenylsilanols"*Organic Letters*. vol. 2, No. 16, pp. 2491-2494. (2000).
Denmark et al., "Highly Stereospecific, Palladium-Catalyzed Cross-Coupling of Alkenylsilanols" *Organic Letters* vol. 2, No. 4, pp. 565-568 (2000).
Dhar, et al., "The TosMIC Approach to 3-(Oxazol-5-yl) Indoles: Application to the Synthesis of Indole-Based IMPDH Inhibitors," Bioorganic & Medicinal Chemistry Letters, 2002.
Eilers et al., "Direct Inhibition of c-Jun N-terminal Kinase in Sympathetic Neurones Prevents c-jun Promoter Activation and NGF Withdrawal-induced Death", *Journal of Neurochemistry*. vol. 76, pp. 1439-1454, 2001.
Eilers et al., "Role of the Jun Kinase Pathway in the Regulation of c-Jun Expression and Apoptosis in Sympathetic Neurons", *The Journal of Neuroscience*. vol. 18, No. 5, pp. 1713-1724, Mar. 1, 1998.
Estus et al., "Aggregated Amyloid-β Protein Induces Cortical Neuronal Apoptosis and Concomitant "Apoptotic" Pattern of Gene Induction", *The Journal of Neuroscience*, vol. 17, No. 20, pp. 7736-7745, Oct. 15, 1997.
Golub et al., Science, vol. 286, pp. 531-537, Oct 15, 1999.
Greene, T. and Wuts, P., *Protective Groups in Organic Synthesis* 3rd Edidtion, Wiley, New York (1999).
Guillard, et al. "Synthesis of New Maltonin Analogues from Dimers of Azaindole and Indole by Use of Suzuki Monocoupling", Heterocycles, vol. 60, No. 4, pp. 865-877 (2003).
Ham et al., "A c-Jun Dominant Negative Mutant Protects Sympathetic Neurons against Programmed Cell Death", *Neuron*, vol. 14, pp. 927-939, May 1995.
Harper and LoGasso, *Drugs of the Future* 2001, 26, 957-973.
Harper et al., "Inhibitors of the JNK Signaling Pathway", *Drugs of the Future*, vol. 26, No. 10, pp. 957-973, 2001.
Hatanaka et al., "Cross-Coupling of Organosilanes with Organic Halides Mediated by Palladium Catalyst and Tris(diethylamino)sulfonium Difluorotrimethylsilicate" *J. Org. Chem* 53 pp. 918-920 (1988).
Hatanaka et al., "Highly Selective Cross-Coupling Reactions of Organosilicon Compounds Mediated by Fluoride Ion and a Palladium Catalyst", *Synlett* pp. 845-853 (1991).
Henry et al, Bioorg. Med. Chem. Lett. 1998, 8, 3335-3340.
Houwing, et al., Preparation of N-Tosylmethylimino Compounds and their Use in the Synthesis of Oxazoles, Imidazoles and Pyrroles, Tetrahedron Letters No. 2, 1976.
International Search Report for PCT/GB2004/002099, mailed Dec. 2, 2004, 4 pages.
International Search Report for PCT/GB2005/000779, mailed Aug. 12, 2005, 4 pages.
Krasnokutskaya et al., *Khim Geterotsikl. Soed* No. 3 pp. 380-384 (1977).
Kruber, Caplus, Copyright 2007 ACS on STN, 2 pages.
Kumar et al, "Synthesis of 7-Azaindole and 7-Azaoxindole Derivatives through a Palladium-Catalyzed Cross Coupling Reaction", J. Org. Chem, 57, pp. 6995-6998 (1992).
Lecointe, Reach-trhough Claims, International Pharmaceutical (2002)(also available at <http:///www.bakerbotts.com/infocenter/publications/detail.aspx?id=bffe4a7d-5beb-4cf8-a189-15a190f0eb>).
Lisnock et al., "Activation of JNK3α1 Requires Both MKK4 and MKK7: Kinetic Characterization of in Vitro Phosphorylated JNK3α1", *Biochemistry*, vol. 39, pp. 3141-3149, 2000.
Littke et al., "Pd/P(t-Bu)$_3$: A Mild and General Catalyst for Stille Reactions of Aryl Chlorides and Aryl Bromides" *J. Am. Chem. Soc.* 124 pp. 6343-6348 (2002).
Littke et al., "Versatile Catalysts for the Suzuki Cross-Coupling of Arylboronic Acids with Aryl and Vinyl Halides and Triflates under Mild Conditions" *J. Am. Chem. Soc.* 122 pp. 4020-4028 (2000).
Martin et al., "Palladium-Catalyzed Cross-Coupling Reactions of Organoboronic Acids with Organic Electrophiles" *Acta Chemica Scandinavica* 47, pp. 221-230 (1993).
Merour et al., Synthesis and Reactivity of 7-Azaindoles (1H-Pyrrolo[2,3-b]pyridine) *Current Organic Chemistry* 5 pp. 471-506 (2001).
Mettey, et al., "Aloisines, a New Family of CDK/GSK-3 Inhibitors. SAR STudy, Crystal Structure in Complex with CDK2, Enzyme Selectivity and Cellular Effects", J. Med. Chem, 46, pp. 222-236 (2003).
Mitchell, T. "Palladium-Catalysed Reactions of Organotin Compounds" *Synthesis* pp. 803-815 (1992).
Park et al, "A FAcile Synthesis of 2,3-Disubstitute Pyrrolo[2,3-b]pyridines via Palladium-Catalyzed Heteroannulation with Internal Alkynes", Tetrahedron Letters 39, pp. 627-630 (1998).
Pisano et al, "Bis-indols: a Novel Class of Molecules Enhancing the Cytodifferentiating Properties of Retinoids in Myeloid Leukemia Cells", Blood, vol. 100, No. 10, pp. 3719-3730 (2002).
Resnick, et al. "Targeting JNK3 for the Treatment of Meurodegenerative Disorders", Drug Discovery Today, Elsevier Science Ltd. 9:21 (2004) pp. 932-939.
Silva, "Reach through Claims: Bust or Boon?", Intellectual Property Update (available at <http://www.dorsey.com/publlications/legal_detail.aspx?FlashNavID=pubs_legal&pubid=170565003>).
Smulik and Diver, "Synthesis of Cyclosporin A-Derived Affinity Reagents by Olefin Metathesis", Organic Letters, vol. 4, No. 12, pp. 2051-2054, 2002.
Stille, J.K., "The Palladium-Catalyzed Cross-Coupling Reactions of Organotin REagents with Organic Electrophiles" *Angew. Chem. Int. Ed. Engl.* 25 pp. 508-524 (1986).
Suzuki, A. "Synthetic Studies via the Cross-Coupling REaction of Organoboron Derivatives with Organic Halides" *Pure Appl. Chem* vol. 63, No. 3 pp. 419-422 (1991).
Tamao et al., "Palladium-Catalyzed Cross-Coupling REaction of Alkenylalkosysilanes with Aryl and Alkenyl Halides in the Presence of a Fluoride Ion" *Tetrahedron Letters*, vol. 30, No. 44 pp. 6051-6054 (1989).
Taylor et al., "Intramolecular Diels-Alder Reactions of 1,2,4-Triazines" *Tetrahedron*, vol. 43, No. 21 pp. 5145-5158 (1987).
Van Leusen, et al., Chapter 3: Synthetic Uses of Tosylmethyl Isocyanide (TosMIC), Organic Reactions, vol. 57, 2001.
Vippagunta et al., "Crystalline Solids", Advanced Drug Delivery Reviews, vol. 48, No. 1; pp. 3-26, 2001.
Watson et al., "Phosphorylation of c-Jun is Necessary for Apoptosis Induced by Survival Signal Withdrawal in Cerebellar Granule Neurons", *The Journal of Neuroscience*, vol. 18, No. 2, pp. 751-762, Jan. 15, 1998.
West, Anthony R., "Solid State Chemistry and its Applications", Wiley, NY 1988.
Witherington et al., "5-Aryl-pyrazolo [3,4-b]pyridines: Potent Inhibitors of Glycogen Synthase Kinase-3 (GSK-3)", Bioorganic & Medicinal Chemistry Letters 13, pp. 1577-1580 (2003).
Young et al., "Pyridinyl Imidazole Inhibitors of p38 Mitogen-activated Protein Kinase Bind in the ATP Site", *The Journal of Biological Chemistry*, vol. 272, No. 18, pp. 12116-12121, May 2, 1997.
Zevaco, T. et al., Bismuth (III) Pyridine—and Pyrazine-Carboxylates, *New J. Chem..*, vol. 15, pp. 927-930, 1991.
Han, Z. et al., "Jun N-Terminal Kinase in Rheumatoid Arthritis," J. of Pharmacol. Exper. Therap. 291(1): 124-130 (1999).
Peng, J. and Andersen, J.K., "The Role of c-Jun N-Terminal Kinase (JNK) in Parkinson's Disease," Life 55(4-5): 267-271, Apr.-May 2003.

\* cited by examiner

JNK INHIBITORS

The present invention relates to novel compounds, their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions.

c-Jun N-terminal kinases (hereinafter referred to as "JNKs") are members of the mitogen-activated protein kinase (MAPK) family. JNKs are involved in response to various stimuli, including proinflammatory cytokines and environmental stress. JNKs, and JNK3 in particular, play an important role during apoptotic death of cells and therefore have been implicated in various disorders including stroke, traumatic brain injury and other neurodegenerative diseases such as Parkinson disease, Alzheimer disease and others. Since JNK activity is a physiological regulator of AP-1 transcriptional activity, JNK inhibitors are expected to reduce inflammatory response.

Apoptosis is a form of cell death in which the cell actively participates in its own destruction in a process involving a characteristic series of biochemical and morphological changes, which are regulated by specific cell death genes. The apoptotic cell death is a process that has been observed in the developing mammalian nervous system. In mice, the inactivation by homologous recombination of genes that encode proteins that promote apoptosis, such as the caspase-3 or the Bax protein, prevents developmental neuronal cell death. The destruction of genes that encode cell death suppressors such as Bcl-x, leads to enhanced neuronal cell death. There is increasing evidence that apoptosis plays an important role in the pathology of acute and chronic neurodegenerative diseases. For example, in transgenic mice overexpressing the anti-apoptotic Bcl-2 protein in the nervous system there is a decrease in infarct volume following cerebral ischemia. Similarly, injection of the caspase inhibitor BAF reduces neuronal cell death following hypoxia/ischaemia in neonatal rats. Another example is spinal muscular atrophy (a motor neuron disease) where loss of function mutations in the SMN gene is associated with the disease. Recent data has shown that the wild type SMN protein binds to Bcl-2 and co-operates with it to inhibit apoptosis. These results suggest that inhibitors of neuronal apoptosis could be beneficial in the treatment of human neurodegenerative diseases. There is increasing evidence that neuronal apoptosis is an important pathological feature of stroke, traumatic brain injury and other neurodegenerative diseases. Therefore, pharmacotherapy using inhibitors of neuronal apoptosis may provide a therapeutic benefit in neurodegenerative conditions.

A number of groups have studied the mechanisms of neuronal cell death using in vitro cell culture systems and the results suggest that in some systems the transcription factor c-Jun is activated by the removal of survival signals and promotes cell death.

Antibodies specific for c-Jun protected NGF-deprived rat sympathetic neurones from apoptosis. Analogous neuroprotection due to expression of a c-Jun dominant negative mutant has been demonstrated, whereas overexpression of wild type c-Jun protein was sufficient to induce apoptosis in the presence of NGF. Estus and co-workers recently showed that an increase in c-Jun RNA levels occurs in cortical neurones undergoing apoptosis after treatment with β-amyloid peptide. It has also been shown that c-Jun is required for apoptosis in cerebellar granule neurones deprived of survival signals.

c-Jun is activated by JNKs, which phosphorylate its transcriptional activation domain. In humans there are three JNK genes: JNK1, JNK2 and JNK3. The RNAs encoding JNK1 and JNK2 are expressed in many tissues, including the brain, but JNK3 is restricted to the nervous system and to a smaller extent the heart and testes.

JNKs are strongly activated in cellular responses to various stresses such as UV radiation, heat shock, osmotic shock, DNA-damaging agents, and proinflammatory cytokines such as TNFα, IL-1β and others. Upstream regulators of the JNK pathway include kinases such as SEK1, MKK7 and MEKK1. There is evidence that Jun kinase activity is required for neuronal apoptosis in vitro. Overexpression of MEKK1 in sympathetic neurones increased c-Jun protein levels and phosphorylation and induced apoptosis in the presence of NGF indicating that activation of the Jun kinase pathway can trigger neuronal cell death. The Jun kinase pathway has been shown to be necessary for the death of differentiated PC12 cells deprived of NGF. Furthermore, compound CEP-1347, which inhibits the c-Jun pathway (upstream of Jun kinase), protects motor neurones against cell death induced by survival factor withdrawal.

In JNK3 homozygous (−/−) knockout mice, epileptic seizures and death of hippocampal CA3 neurones induced by injection of kainic acid is blocked. This indicates that JNK3 is involved in certain forms of neuronal cell death in vivo. It is also a critical component of GluR6-mediated excitotoxicity. Furthermore, JNK3 (−/−) mice appear to develop normally and are viable suggesting that JNK3 is not essential for development or viability.

Strong nuclear JNK3 immunoreactivity in the brain CA1 neurones of patients with acute hypoxia suggests that JNK3 is involved in hypoxia-related neurodegeneration. Transient hypoxia, may also trigger apoptosis through JNK signaling pathway in developing brain neurones.

Furthermore, JNK3 immunoreactivity is colocalized with Alzheimer disease-affected neurones. Moreover JNK3 is related to neurofibrillary pathology of Alzheimer disease. In particular, JNK3 induces robust phosphorylation of amyloid precursor protein (APP) thus affecting its metabolism in disease state.

The present inventors have provided compounds, which are inhibitors of c-Jun N-terminal kinases.

The first aspect of the invention therefore relates to a compound of formula (I) as illustrated below:

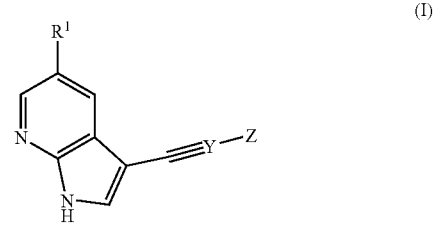

(I)

wherein $R^1$ is an optionally substituted $C_{3-12}$ carbocyclyl or $C_{3-12}$ heterocyclyl group, Y is N or C and Z is lone electron pair, hydrogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $(CH_2)_nOR^2$, $(CH_2)_nNR^2{}_2$, $CO_2R^2$, $COR^2$, $CONR^2{}_2$, wherein the $C_{1-12}$ alkyl group optionally contains one or more insertions selected from —O—, —N($R^2$)— —S—, —S(O)— and —S($O_2$)—; and each substitutable nitrogen atom in Z is optionally substituted by $R^3$, $COR^3$, $SO_2R^3$ or $CO_2R^3$;

wherein n is 1 to 6, preferably n is 1, 2 or 3;

wherein $R^2$ is hydrogen, $C_{1-12}$ alkyl, $C_{3-12}$ carbocyclyl or $C_{3-12}$ heterocyclyl, $C_{1-12}$alkyl$C_{3-16}$carbocyclyl or $C_{1-12}$alkyl$C_{3-12}$heterocyclyl optionally substituted by one or more of $C_{1-6}$ alkyl, halogen, $C_{1-6}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4{}_2$, $S(O)_2R^4$, $SONR^4{}_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N($R^4$)—, —S(O)— and —S($O_2$)—, wherein each $R^4$ may be the same or different and is as defined below;

wherein two $R^2$ in $NR^2{}_2$ may form a partially saturated, unsaturated or fully saturated five to seven membered ring containing one to three heteroatoms, optionally and independently substituted with one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $OR^5$, $SR^5$, $NO_2$, CN, $NR^5{}_2$, $NR^5COR^5$, $NR^5CONR^5{}_2$, $NR^5COR^5$, $NR^5CO_2R^5$, $CO_2R^5$, $COR^5$, $CONR^5{}_2$, $S(O)_2R^5$, $SONR^5{}_2$, $S(O)R^5$, $SO_2NR^5{}_2$, or $NR^5S(O)_2R^5$; and each saturated carbon in the optional ring is further optionally and independently substituted by =O, =S, $NNR^6{}_2$, =N—$OR^6$, =$NNR^6COR^6$, =$NNR^6CO_2R^6$, =$NNSO_2R^6$, or =$NR^6$;

wherein $R^3$ is hydrogen, $C_{1-6}$ alkyl, $C_{1-6}$ haloalkyl, or $C_{6-12}$ aryl;

wherein $R^4$ is hydrogen, $C_{1-6}$ alkyl, $C_{1-6}$ haloalkyl or $C_{6-12}$ aryl;

wherein $R^5$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^7$, $SR^7$, $NO_2$, CN, $NR^7R^7$, $NR^7COR^7$, $NR^7CONR^7R^7$, $NR^7COR^7$, $NR^7CO_2R^7$, $CO_2R^7$, $COR^7$, $CONR^7{}_2$, $S(O)_2R^7$, $SONR^7{}_2$, $S(O)R^7$, $SO_2NR^7R^7$, $NR^7S(O)_2R^7$, wherein the $C_{1-12}$ alkyl group optionally incorporates one or two insertions selected from the group consisting of —O—, —N($R^7$)—, —S(O)— and —S($O_2$)—, wherein each $R^7$ may be the same or different and is as defined below;

wherein $R^6$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^7$, $SR^7$, $NO_2$, CN, $NR^7R^7$, $NR^7COR^7$, $NR^7CONR^7R^7$, $NR^7COR^7$, $NR^7CO_2R^7$, $CO_2R^7$, $COR^7$, $CONR^7{}_2$, $S(O)_2R^7$, $S(O)R^7$, $SO_2NR^7R^7$, $NR^7S(O)_2R^7$, wherein the $C_{1-12}$ alkyl group optionally incorporates one or two insertions selected from the group consisting of —O—, —N($R^7$)—, —S(O)— and —S($O_2$)—, wherein each $R^7$ may be the same or different and is as defined below;

wherein $R^7$ is hydrogen, $C_{1-6}$ alkyl, or $C_{1-6}$ haloalkyl wherein the optionally substituted carbocyclyl or heterocyclyl group in $R^1$ and Z is optionally and independently fused to a partially saturated, unsaturated or fully saturated five to seven membered ring containing zero to three heteroatoms, and each substitutable carbon atom in $R^1$ or Z, including the optional fused ring, is optionally and independently substituted by one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $(CH_2)_nOR^{12}$, $(CH_2)_nNR^{12}{}_2$, $OR^{12}$, $SR^{12}$, $NO_2$, CN, $NR^{12}{}_2$, $NR^{12}COR^{12}$, $NR^{12}CONR^{12}{}_2$, $NR^{12}COR^{12}$, $NR^{12}CO_2R^{12}$, $CO_2R^{12}$, $COR^{12}$, $CONR^{12}{}_2$, $S(O)_2R^2$, $SONR^{12}{}_2$, $S(O)R^{12}$, $SO_2NR^{12}{}_2$, or $NR^{12}S(O)_2R^{12}$ wherein the $C_{1-12}$ alkyl group optionally contains one or more insertions selected from —O—, —N($R^{12}$)— —S—, —S(O)— and —S($O_2$)—; and each saturated carbon in the optional fused ring is further optionally and independently substituted by =O, =S, $NNR^{13}{}_2$, =N—$OR^{13}$, =$NNR^{13}COR^{13}$, =$NNR^{13}CO_2R^{13}$, =$NNSO_2R^3$, or =$NR^{13}$; and each substitutable nitrogen atom in $R^1$ is optionally substituted by $R^{14}$, $COR^{14}$, $SO_2R^{14}$ or $CO_2R^{14}$;

wherein n is 1 to 6, preferably n is 1, 2 or 3;

wherein $R^{12}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{15}$, $SR^{15}$, $NO_2$, CN, $NR^{15}R^{15}$, $NR^{15}COR^{15}$, $NR^{15}CONR^{15}R^{15}$, $NR^{15}COR^{15}$, $NR^{15}CO_2R^{15}$, $CO_2R^{15}$, $COR^{15}$, $CONR^{15}{}_2$, $S(O)_2R^{15}$, $SONR^{15}{}_2$, $S(O)R^{15}$, $SO_2NR^{15}R^{15}$, $NR^{15}S(O)_2R^{15}$, wherein the $C_{1-12}$ alkyl group optionally incorporates one or two insertions selected from the group consisting of —O—, —N($R^{15}$)—, —S(O)— and —S($O_2$)—, wherein each $R^{15}$ may be the same or different and is as defined below;

wherein two $R^{12}$ in $NR^{12}{}_2$ may form a partially saturated, unsaturated or fully saturated five to seven membered ring containing one to three heteroatoms, optionally and independently substituted with one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $OR^{16}$, $SR^{16}$, $NO_2$, CN, $NR^{16}{}_2$, $NR^{16}COR^{16}$, $NR^{16}CONR^{16}{}_2$, $NR^{16}COR^{16}$, $NR^{16}CO_2R^{16}$, $CO_2R^{16}{}_7$, $COR^{16}$, $CONR^{16}{}_2$, $S(O)_2R^{16}$, $SONR^{16}{}_2$, $S(O)R^{16}$, $SO_2NR^{16}{}_2$, or $NR^{16}S(O)_2R^{16}$; and each saturated carbon in the optional ring is further optionally and independently substituted by =O, =S, $NNR^{17}{}_2$, =N—$OR^{17}$, =$NNR^{17}COR^{17}$, =$NNR^{17}CO_2R^{17}$, =$NNSO_2R^{17}$, or =$NR^{17}$;

wherein $R^{13}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{15}$, $SR^{15}$, $NO_2$, CN, $NR^{15}R^{15}$, $NR^{15}COR^{15}$, $NR^{15}CONR^{15}R^{15}$, $NR^{15}CORR^{15}$, $NR^{15}CO_2R^{15}$, $CO_2R^{15}$, $COR^{15}$, $CONR^{15}{}_2$, $S(O)_2R^{15}$, $S(O)R^{15}$, $SO_2NR^{15}R^{15}$, $NR^{15}S(O)_2R^{15}$, wherein the $C_{1-12}$ alkyl group optionally incorporates one or two insertions selected from the group consisting of —O—, —N($R^{15}$)—, —S(O)— and —S($O_2$)—, wherein each $R^{15}$ may be the same or different and is as defined below;

wherein $R^{14}$ is hydrogen, $C_{1-6}$ alkyl, $C_{1-6}$ haloalkyl, or $C_{6-12}$ aryl;

wherein $R^{15}$ is hydrogen, $C_{1-6}$ alkyl, or $C_{16}$ haloalkyl;

wherein $R^{16}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{18}$, $SR^{18}$, $NO_2$, CN, $NR^{18}R^{18}$, $NR^{18}COR^{18}$, $NR^{18}CONR^{18}R^{18}$, $NR^{18}COR^{18}$, $NR^{18}CO_2R^{18}$, $CO_2R^{18}$, $COR^{18}$, $CONR^{18}{}_2$, $S(O)_2R^{18}$, $SONR^{18}{}_2$, $S(O)R^{18}$, $SO_2NR^{18}R^{18}$, $NR^{18}S(O)_2R^{18}$, wherein the $C_{1-12}$ alkyl group optionally incorporates one or two insertions selected from the group consisting of —O—, —N($R^{18}$)—, —S(O)— and —S($O_2$)—, wherein each $R^{18}$ may be the same or different and is as defined below;

wherein $R^{17}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{18}$, $SR^{18}$, $NO_2$, CN, $NR^{18}R^{18}$, $NR^{18}COR^{18}$, $NR^{18}CONR^{18}R^{18}$, $NR^{18}COR^{18}$, $NR^{18}CO_2R^{18}$, $CO_2R^{18}$, $COR^{18}$, $CONR^{18}{}_2$, $S(O)_2R^{18}$, $S(O)R^{18}$, $SO_2NR^{18}R^{18}$, $NR^{18}S(O)_2R^{18}$, wherein the $C_{1-12}$ alkyl group optionally incorporates one or two insertions selected from the group consisting of —O—, —N($R^{18}$)—, —S(O)— and —S($O_2$)—, wherein each $R^{18}$ may be the same or different and is as defined below;

wherein $R^{18}$ is hydrogen, $C_{1-6}$ alkyl, or $C_{1-6}$ haloalkyl and the pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

For the avoidance of doubt when a group as defined above contains two or more radicals e.g. the radical $R^{13}$ as for example in the groups $SO_2NR^{13}R^{13}$ and $NR^{13}COR^{13}$, the two or more radicals, e.g. $R^{13}$, may be the same or different.

For the purposes of all aspects of this invention, alkyl relates to both straight chain and branched alkyl radicals of 1 to 12 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. In particular, alkyl relates to a group having 1, 2, 3, 4, 5, 6, 7, 8, 9, 10, 11 or 12 carbon atoms. The term alkyl also encompasses cycloalkyl radicals including but not limited to cyclopropyl, cyclobutyl, $CH_2$-cyclopropyl, $CH_2$-cyclobutyl, cyclopentyl or cyclohexyl. In particular, cycloalkyl relates to a group having 3, 4, 5, 6, 7, 8, 9, 10, 11 or 12 carbon atoms. Cycloalkyl groups may be optionally substituted or fused to one or more carbocyclyl or heterocyclyl group. Haloalkyl relates to an alkyl radical as defined above preferably having 1 to 8 carbon atoms, preferably 1 to 4 carbon atoms substituted with one or more halide atoms for example one or more of F, Cl, Br or I, such as $CH_2CH_2Br$, $CF_3$ or $CCl_3$.

The term "alkenyl" means a straight chain or branched alkylenyl radical of 2 to 12 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. In particular, alkenyl relates to a group having 2, 3, 4, 5, 6, 7, 8, 9, 10, 11 or 12 carbon atoms. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc. In particular, alkynyl relates to a group having 2, 3, 4, 5, 6, 7, 8, 9, 10, 11 or 12 carbon atoms.

"Carbocyclyl" relates to a saturated, partly unsaturated or unsaturated 3-12 membered hydrocarbon ring, preferably a 6-12 membered hydrocarbon ring, including cycloalkyl and aryl.

"Aryl" means an aromatic 3-12 membered hydrocarbon preferably a 6-12 membered hydrocarbon containing one ring or being fused to one or more saturated or unsaturated rings including but not limited to phenyl, napthyl, anthracenyl or phenantrracenyl.

"Heteroaryl" means an aromatic 3-12 membered aryl preferably a 5-12 membered aryl containing one or more heteroatoms selected from N, O or S and containing one ring or being fused to one or more saturated or unsaturated rings and;

"Heterocyclyl" means a 3-12 membered ring system preferably a 5-12 membered aryl containing one or more heteroatoms selected from N, O or S and includes heteroaryl. In particular, the terms "carbocyclyl", "aryl", "heteroaryl" and "heterocyclyl" relate to a group having 3, 4, 5, 6, 7, 8, 9, 10, 11 or 12 carbon atoms.

The heterocyclyl system can contain one ring or may be fused to one or more saturated or unsaturated rings; the heterocyclyl can be fully saturated, partially saturated or unsaturated and includes but is not limited to heteroaryl and heterocarbocyclyl. Examples of carbocyclyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, or trithiane.

For the purpose of the present invention, the term "fused" includes a polycyclic compound in which one ring contains one or more atoms preferably one, two or three atoms in common with one or more other ring.

Halogen means F, Cl, Br or I, preferably Br and F.

$R^1$ is preferably a five or six membered carbocyclyl or heterocyclyl group wherein the carbocyclyl or heterocyclyl group is optionally fused to one or more unsaturated rings.

$R^1$ is preferably selected from phenyl, cyclohexyl, acridine, benzimidazole, benzofuran, benzothiophene, benzoxazole, benzothiazole, furan, imidazole, indole, isoindole, isoquinoline, isoxazole, isothiazole, morpholine, napthaline, oxazole, phenazine, phenothiazine, phenoxazine, piperazine, piperidine, pyrazole, pyridazine, pyridine, pyrrole, quinoline, quinolizine, tetrahydrofuran, tetrazine, tetrazole, thiophene, thiazole, thiomorpholine, thianaphthalene, thiopyran, triazine, triazole, or trithiane.

More preferably $R^1$ is phenyl, thiophene or pyridinyl.

As discussed above, $R^1$ can be optionally substituted at any position on the carbocyclyl, heterocyclyl or optional fused ring.

Substitution can occur at the ortho, meta or para positions relative to the pyridine ring. When $R^1$ is a six-membered ring, substitution is preferably at the ortho and/or para positions, more preferably at the ortho position.

$R^1$ is preferably substituted with one or more of $OR^{12}$, $NR^{12}_2$, $SR^{12}$, $(CH_2)_nOR^{12}$, $(CH_2)_nNR^{12}_2$, halogen, $C_{1-6}$ alkyl, $C_{2-6}$ alkenyl, $C_{2-6}$ alkynyl, $C_{1-6}$ haloalkyl, $NO_2$, CN, $CO_2R^{12}$, $COR^{12}$, $CONR^{12}_2$, $S(O)_2R^{12}$, $S(O)R^{12}$ or $SO_2NR^{12}_2$;

wherein $R^{12}$ is hydrogen, $C_{1-4}$ alkyl, $C_{5-12}$ heterocyclyl or $C_{6-12}$ aryl preferably phenyl, and n is 1, 2, 3, 4, 5 or 6, and each substitutable nitrogen atom in $R^1$ is optionally substituted by $R^{14}$, $COR^{14}$, $SO_2R^{14}$ or $CO_2R^{14}$; wherein $R^{14}$ is $C_{1-6}$ alkyl, $C_{1-6}$ haloalkyl, or $C_{6-12}$ aryl;

Representative compounds according to the first aspect of the invention are illustrated below

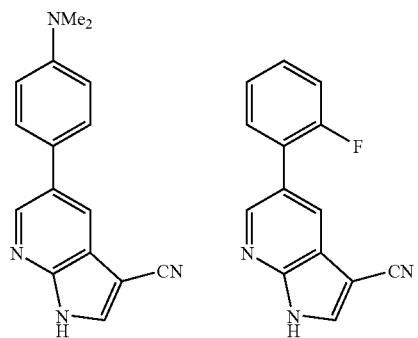

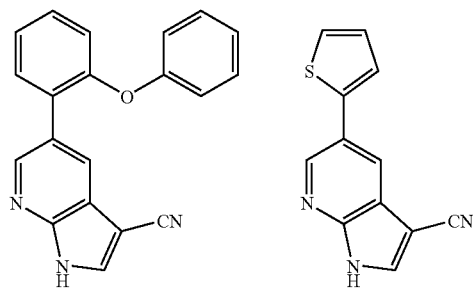
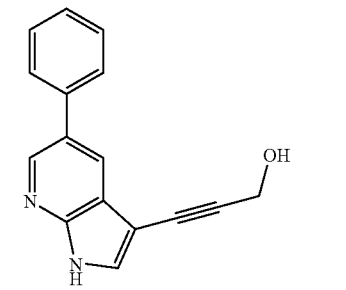
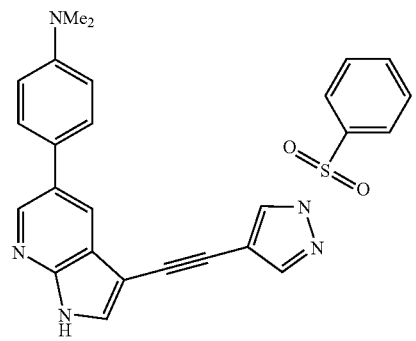
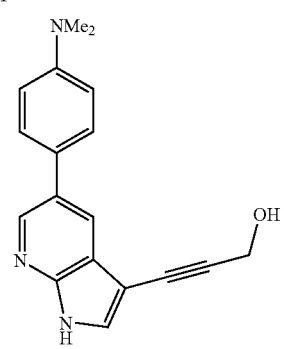
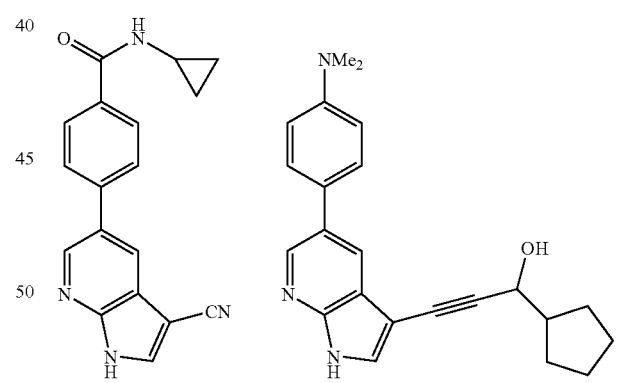
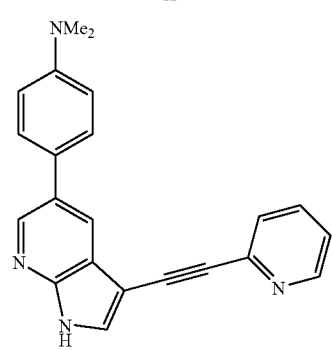

-continued

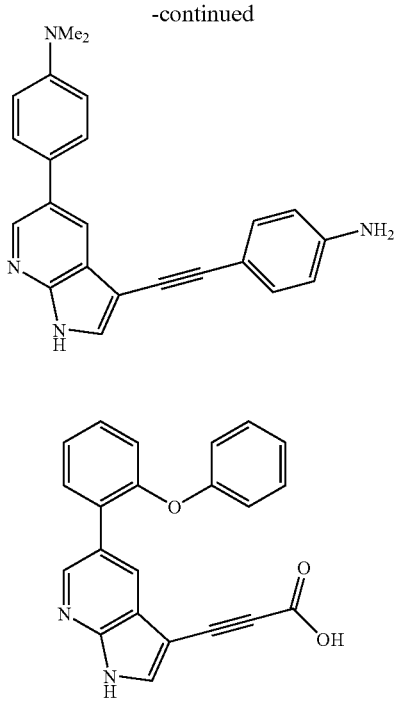

The compounds of the first aspect may be provided as a salt, preferably as a pharmaceutically acceptable salt of compounds of formula (I). Examples of pharmaceutically acceptable salts of these compounds include a hydrate and those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases, which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms. The compounds of the invention may exist in trans or cis form. The first aspect of the invention covers all of these compounds.

The second aspect of the invention provides a process for the manufacture of a compound of formula (I) as defined in the first aspect of the invention wherein a compound of formula (III) is converted to a compound of formula (I) by the removal of the group $R^{20}$.

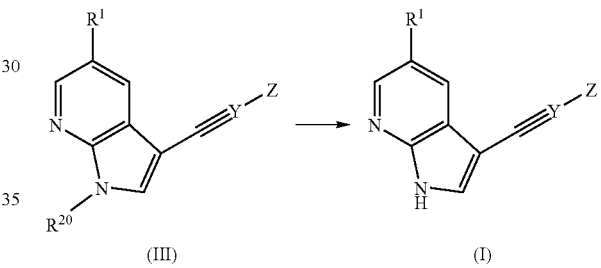

wherein $R^1$, Y and Z are as defined in the first aspect of the invention and $R^{20}$ is an amino protecting group.

Protection of the pyrrole nitrogen can be carried out by any suitable protecting group known in the art. Preferably $R^{20}$ is $R^{30}SO_2$, $R^{30}C(O)$, $(R^{30}_3Si$, $R^{30}OCH_2$, $(R^{30})_2NSO_2$, $R^{30}OC(O)$, $R^{30}(R^{30}O)CH$, $R^{30}CH_2CH_2$, $R^{30}CH_2$, $PhC(O)CH_2$, $CH_2$=CH, $ClCH_2CH_2$, $Ph_3C$, $Ph_2$(4-pyridyl)C, $Me_2N$, $HO$—$CH_2$, $R^{30}OCH_2$, $(R^{30})SiOCH_2$, $(R^{30}O)_2CH$, t-BuOC(O)CH_2$, $Me_2NCH_2$ or tetrahydropyranylamine, wherein $R^{30}$ is $C_{1-6}$ alkyl or $C_{6-12}$ aryl, preferably methyl, ethyl, propyl, butyl, phenyl or naphthyl.

The conditions for the removal of the group $R^{20}$ will depend on the identity of the $R^{20}$ group. For example, when $R^{20}$ is sulfonamide, the compound of formula (I) can be produced by the treatment of the compound of formula (III) under basic conditions, for instance using sodium hydroxide in water/ethanol.

Preferably $R^{20}$ is sulfonamide, more preferably $(R^{30})_2NSO_2$, most preferably benzenesulfonamide.

A compound of formula (I) may undergo one or more further reactions to provide a different compound of formula (I). For example, a compound may undergo a reduction, oxidation, elimination, substitution and/or addition reaction. In particular, a compound of formula (I) may undergo a Stille reaction, which can be carried out according to Stille (*Angew. Chem., Int. ed, Engl.* 1986, 25, 508; Mitchell *Synthesis*, 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020), or Hiyama reaction which can be carried out according to Hatanaka et al. *J. Org. Chem.* 1988, 53, 918, Hatanaka et al. *Synlett,* 1991, 845, Tamao et al. *Tetrahedron Lett.* 1989, 30, 6051 or Denmark et al. *Org. Lett.* 2000, 2, 565, ibid. 2491.

The third aspect of the invention provides a compound of formula (III)

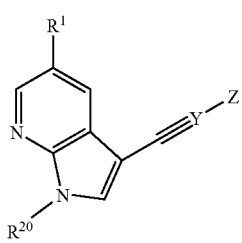

wherein $R^1$, Y and Z are as defined in the first aspect and $R^{20}$ is a nitrogen protecting group defined in the second aspect of the invention.

The fourth aspect of the invention provides a process for the formation of a compound of formula (III) by the palladium catalyzed introduction of the group C≡Y-Z into compound (II).

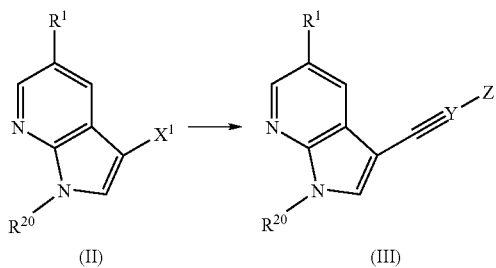

wherein $R^1$ is as defined for the first aspect wherein $R^{20}$ is an amino protecting group, such as $R^{30}SO_2$, $R^{30}C(O)$, $R^{30}{}_3Si$, $R^{30}OCH_2$, $(R^{30})_2NSO_2$, $R^{30}OC(O)$, $R^{30}(R^{30}O)CH$, $R^{30}CH_2CH_2$, $R^{30}CH_2$, $PhC(O)CH_2$, $CH_2$=CH, $ClCH_2CH_2$, $Ph_3C$, $Ph_2(4$-pyridyl$)C$, $Me_2N$, $HO—CH_2$, $R^{30}OCH_2$, $(R^{30})_3SiOCH_2$, $(R^{30})_2CH$, t-BuOC(O)CH$_2$, $Me_2NCH_2$, or tetrahydropyranylamine, wherein $R^{30}$ is $C_{1-6}$ alkyl or $C_{6-12}$ aryl, and wherein $X^1$ is F, Cl, Br I or $CF_3SO_3$ preferably I or Br.

More preferably $R^{20}$ is sulfonamide, most preferably benzenesulfonamide or $(R^{30})_2NSO_2$.

When Y is N, compound (II) can be reacted under standard cyanation conditions (Sakamoto, T. and Ohsawa, K. *J. Chem. Soc. Perkin Trans.* 1, 1999, 2323) to produce the compound of formula (III, Y=N).

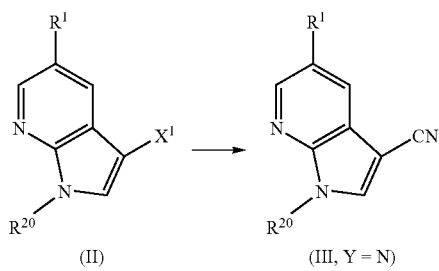

Preferably, the compound of formula (III, Y=N) can be produced from a compound of formula (II) by incubation with CuCN, 1,1'-bis(diphenylphosphino)ferrocene (dppf) and a palladium catalyst such as tris(dibenzylideneacetone) dipalladium

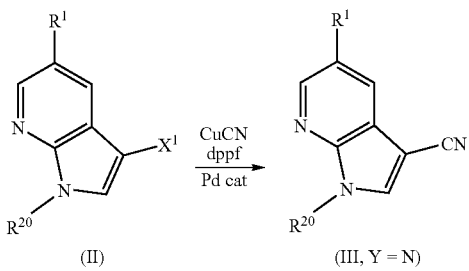

When Y is C, compound (II) can be reacted with an acetylene derivative H—C≡C-Z under conditions similar to those used by Minakata et al. (*Bull. Chem. Soc. Jpn.* 1992, 65, 2992) to produce a compound of formula (III, Y=C).

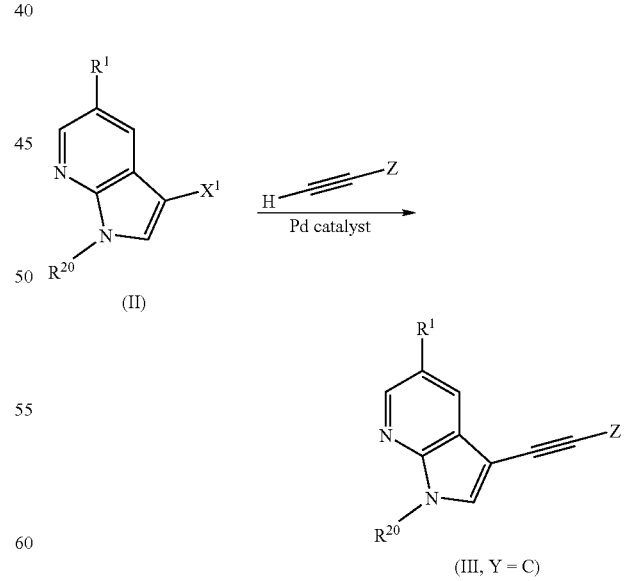

Preferably the compound of formula (III, Y=C) can be produced from a compound of formula (II) and acetylene H—C≡C-Z by incubation with $PdCl_2(PPh_3)_2$ and CuI.

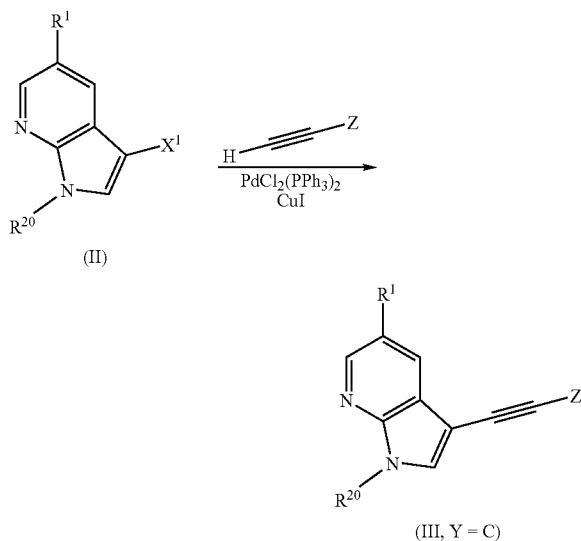

(II)

(III, Y = C)

Methods for producing compound of formula (II) are disclosed in GB0305144.8.

A compound of formula (III) may undergo one or more further reactions to provide a different compound of formula (III). For example, a compound may undergo a reduction, oxidation, elimination, substitution and/or addition reaction. In particular, a compound of formula (III) may undergo a Stille reaction, which can be carried out according to Stille (*Angew. Chem., Int. ed, Engl.* 1986, 25, 508; Mitchell *Synthesis*, 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020), or Hiyama reaction which can be carried out according to Hatanaka et al. *J. Org. Chem.* 1988, 53, 918, Hatanaka et al. *Synlett*, 1991, 845, Tamao et al. *Tetrahedron Lett.* 1989, 30, 6051, or Denmark et al. *Org. Lett.* 2000, 2, 565, ibid. 2491.

The fifth aspect of the invention provides a process for the manufacture of a compound of formula (III) as defined in the third aspect of the invention comprising a a) reaction of a compound of formula (IV) with stannane $R^1$—$Sn(R^{31})_3$ in the presence of a palladium catalyst or b) reaction of a compound of formula (IV) with boronic acid or ester $R^1$—$B(OR^{32})_2$ in a presence of a suitable palladium catalyst or c) reaction of a compound of formula (IV) with silane $R^1$—$Si(R^{31})_3$ in the presence of a palladium catalyst

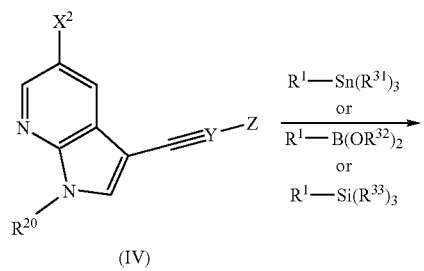

(IV)

-continued

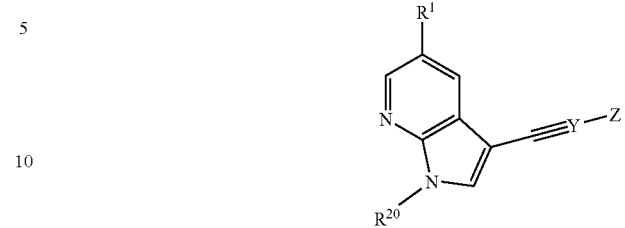

(III)

wherein $R^1$, Y and Z are as defined in the first aspect, $X^2$ is a halide, preferably selected from Cl, Br or I, more preferably Br and $R^{20}$ is a nitrogen protecting group as defined in the second aspect of the invention;

wherein each of $R^{31}$ is independently $C_{1-6}$ alkyl, wherein each of $R^{32}$ is independently hydrogen or $C_{1-6}$ alkyl or wherein two $R^{32}$ groups together form a five, six or seven membered optionally ring with the boron and oxygen atoms, wherein the ring is optionally substituted with one or more $C_{1-6}$ alkyl group preferably methyl or ethyl. Preferably, $R^{32}$ is hydrogen or both $R^{32}$ groups form the group —$C(CH_3)_2$—$C(CH_3)_2$—.

wherein $R^{33}$ is independently $C_{1-6}$ alkyl, F, OH

Suitable catalysts for the purpose of this invention include $(PPh_3)_2PdCl_2$ or $(PPh_3)_4Pd$, $Pd(OAc)_2$, $[PdCl(\eta^3-C_3H_5]_2$, $Pd_2(dba)_3$ (wherein dba=dibenzylidenacetone), Pd/P(t-Bu)$_3$ It will be appreciated that the reaction set out as option a) for the fifth aspect is a Stille reaction, which can be carried out according to Stille *Angew. Chem., Int. ed, Engl.* 1986, 25, 508; Mitchell *Synthesis*, 1992, 803 or Littke et al. (*J. Am. Chem. Soc.* 2002, 124, 6343), The reaction set out as option b) for the fifth aspect is a Suzuki reaction which can be carried out according to Suzuki (*Pure Appl. Chem.* 1991, 63, 419) or Littke et al. (*J. Am. Chem. Soc.* 2000, 122, 4020).

It will be appreciated that the reaction set out as option c) for the fifth aspect is a Hiyama reaction which can be carried out according to Hatanaka et al. *J. Org. Chem.* 1988, 53, 918, Hatanaka et al. *Synlett*, 1991, 845, Tamao et al. *Tetrahedron Lett.* 1989, 30, 6051, or Denmark et al. *Org. Lett.* 2000, 2, 565, ibid. 2491.

The sixth aspect of the invention provides a process for the manufacture of compound of formula (I) as defined in the first aspect of the invention comprising a a) reaction of a compound of formula (V) with stannane $R^1$—$Sn(R^{31})_3$ in the presence of a palladium catalyst or b) reaction of a compound of formula (V) with boronic acid or ester $R^1$—$B(OR^{32})_2$ in a presence of a suitable palladium catalyst or c) reaction of a compound of formula (V) with silane $R^1$—$Si(R^{31})_3$ in the presence of a palladium catalyst

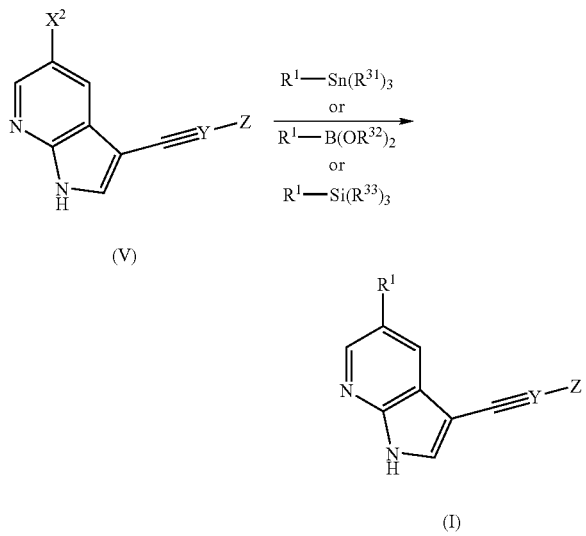

(I)

wherein $X^2$ is as defined in the fifth aspect,
wherein $R^1$, Y and Z are as defined in the first aspect, and
wherein each of $R^{31}$, $R^{32}$, or $R^{33}$ are as defined in the fifth aspect Suitable catalysts for the purpose of this invention include $(PPh_3)_2PdCl_2$ or $(PPh_3)_4Pd$, $Pd(OAc)_2$, $[PdCl(\eta^3-C_3H_5)]_2$, $Pd_2(dba)_3$ (wherein dba=dibenzylideneacetone), $Pd/P(t-Bu)_3$ It will be appreciated that the reaction set out as option a) for the sixth aspect is a Stille reaction, which can be carried out according to Stille *Angew. Chem., Int. ed, Engl.* 1986, 25, 508; Mitchell *Synthesis*, 1992, 803 or Littke et al. (*J. Am. Chem. Soc.* 2002, 124, 6343).

The reaction set out as option b) for the sixth aspect is a Suzuki reaction which can be carried out according to Suzuki (*Pure Appl. Chem.* 1991, 63, 419) or Littke et al. (*J. Am. Chem. Soc.* 2000, 122, 4020).

It will be appreciated that the reaction set out as option c) for the sixth aspect is a Hiyama reaction which can be carried out according to Hatanaka et al. *J. Org. Chem.* 1988, 53, 918, Hatanaka et al. *Synlett,* 1991, 845, Tamao et al. *Tetrahedron Lett.* 1989, 30, 6051, or Denmark et al. *Org. Lett.* 2000, 2, 565, ibid. 2491.

The seventh aspect provides a compound of formula (V)

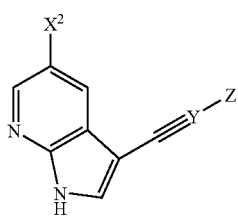

(V)

wherein Y and Z are as defined in the first aspect
wherein $X^2$ is as defined in the fifth aspect, preferably $X^2$ is bromide.

The eighth aspect of the invention provides a process for the manufacture of a compound of formula (V) as defined in the seventh aspect of the invention comprising the conversion of a compound of formula (IV) into a compound of formula (V) by removal of the group $R^{20}$,

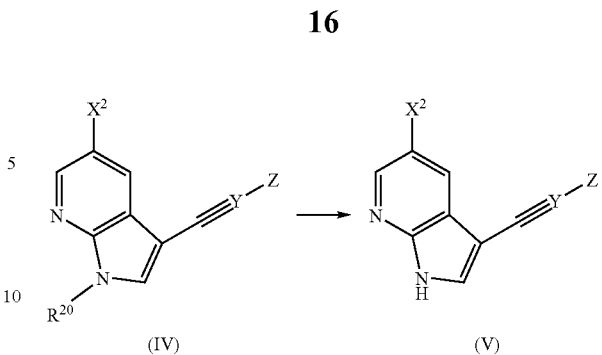

wherein Y and Z are as defined in the first aspect
wherein $X^2$ is as defined in the fifth aspect and
wherein $R^{20}$ is as defined in the second aspect The conditions for the removal of the group $R^{20}$ will depend on the identity of the $R^{20}$ group. For example, when $R^{20}$ is sulfonamide, the compound of formula (V) can be produced by the treatment of the compound of formula (IV) under basic conditions, for instance using sodium hydroxide in water/ethanol.

The ninth aspect of the invention provides a compound of formula (IV)

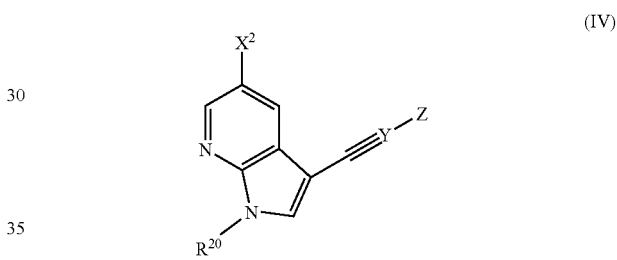

(IV)

wherein Y and Z are as defined in the first aspect
wherein $R^{20}$ is as defined in the second aspect and
wherein $X^2$ is as defined in the fifth aspect The tenth aspect of the invention provides a process for the manufacture of a compound of formula (VII) comprising the reaction of aldoxime (VI) with selenium dioxide,

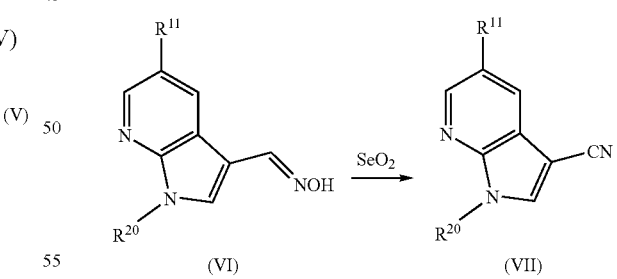

wherein $R^{11}$ is $X^2$ or $R^1$
wherein $X^2$ is as defined in the fifth aspect and
wherein $R^1$ is defined in the first aspect;
wherein $R^{20}$ is a nitrogen protecting group as defined in the second aspect of the invention.

It will be appreciated that when $R^{11}$ is a group as defined for $R^1$ the process of the tenth aspect provides a compound of formula (III), (i.e. the compound of formula (VII) corresponds to the compound of formula III, wherein Y=N). The tenth aspect of the invention therefore also encompasses a process for the manufacture of a compound of formula III, (Y=N) from the aldoxime of formula (VI).

It will be appreciated that when $R^{11}$ is a group as defined for $X^2$ the process of the tenth aspect of the invention produces a compound of formula (IV) (i.e. a compound of formula (VII) corresponds to the compound of formula IV, Y=N). The tenth aspect of the invention therefore also encompasses a process for the manufacture of a compound of formula IV, (Y=N) from the aldoxime of formula (VI).

The eleventh aspect of the invention provides a compound of formula (VI)

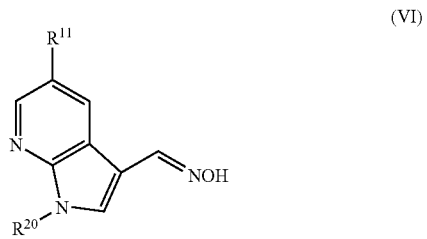

(VI)

wherein $R^{11}$ is as defined in the tenth aspect, and $R^{20}$ is a nitrogen protecting group defined in the second aspect of the invention.

The invention encompasses both cis and trans isomers of (VI) and a mixture of isomers of (VI).

The twelfth aspect of the invention provides a process for the manufacture of a compound of formula (VI) as defined in the eleventh aspect of the invention comprising the reaction of aldehyde (VIII) with hydroxylamine,

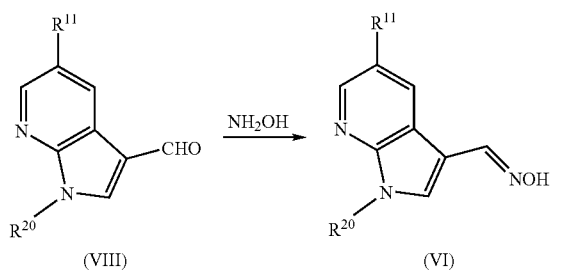

wherein $R^{11}$ is as defined in the tenth aspect and $R^{20}$ is a nitrogen protecting group as defined in the second aspect of the invention.

The compound of formula (VI) can be generated in situ by the process of the twelfth aspect, and further reacted with selenium dioxide as set out in the tenth aspect. The compound of formula (VII) can therefore be produced from the compound of formula (VI) via the compound of formula (VI) by the reaction of a compound of formula (VIII) with hydroxylamine to give a compound of formula (VI) as set out in the twelfth aspect, followed by the subsequent reaction of the aldoxime (VI) with selenium dioxide to give a compound of formula (VII) as set out in the tenth aspect. Alternatively the compound of formula (VII) can be produced from a compound of formula (VIII) in a "one pot" synthesis under conditions similar to those used by Sosnovsky et al. (Synthesis, 1979, 722).

A compound of formula (VI) may undergo one or more further reactions to provide a different compound of formula (VI). For example, a compound may undergo a reduction, oxidation, elimination, substitution and/or addition reaction. In particular, a compound of formula (VI) may undergo a Stille reaction, which can be carried out according to Stille (*Angew. Chem., Int. ed, Engl.* 1986, 25, 508; Mitchell *Synthesis*, 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020).

The thirteenth aspect of the invention provides a compound of formula (VIII)

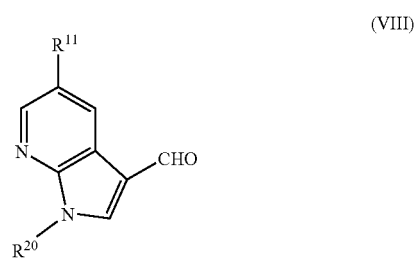

(VIII)

wherein $R^{11}$ is as defined in the tenth aspect, and wherein $R^{20}$ is a nitrogen protecting group as defined in the second aspect of the invention.

The fourteenth aspect of the invention provides a process for the manufacture of a compound of formula (VIII) as defined in the thirteenth aspect of the invention by the addition of the $R^{20}$ group to a compound of general formula (IX).

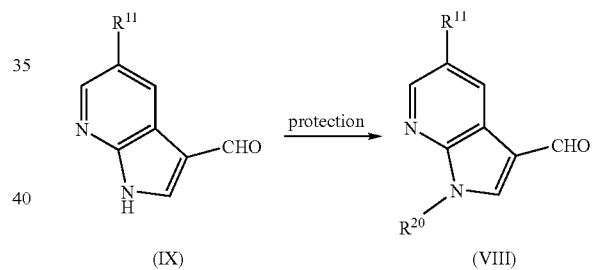

Conditions for the introduction of the protecting group $R^{20}$ will depend upon the protecting group used. Compound (VIII) can be produced by the initial formation of the relevant salt, for example by treatment with NaH in DMF, followed by reaction of the salt with an electrophile such as sulfonyl halide, acid chloride. Alternatively a compound of formula (VIII) can be produced by the direct reaction of compound (IX) with an electrophile such as benzensulfonyl halide, preferably benzenesulfonyl chloride. This reaction is preferably carried out in the presence of base (such as sodium hydroxide) and a phase transfer catalyst such as tetra-n-butylammonium bromide or tetra-n-butylammonium hydrogen sulphate.

A compound of formula (VII) may undergo one or more further reactions to provide a different compound of formula (VIII). For example, a compound may undergo a reduction, oxidation, elimination, substitution and/or addition reaction. In particular, a compound of formula (VIII) may undergo a Stille reaction, which can be carried out according to Stille (*Angew. Chem., Int. ed, Engl.* 1986, 25, 508; Mitchell *Synthesis*, 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020).

The fifteenth aspect of the invention provides a compound of formula (IX)

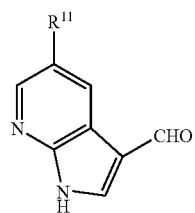

(IX)

wherein $R^{11}$ is as defined in the tenth aspect.

The sixteenth aspect of the invention provides a process for the manufacture of a compound of formula (IX) as defined in the fifteenth aspect of the invention by the reaction of a compound of a formula (X) with hexamethylenetetramine in aqueous propionic acid. Preferably the reaction is carried out under the conditions similar to those used by Robison, M. M. and Robison, B. L. (*J. Am. Chem. Soc.* 1955, 77, 457).

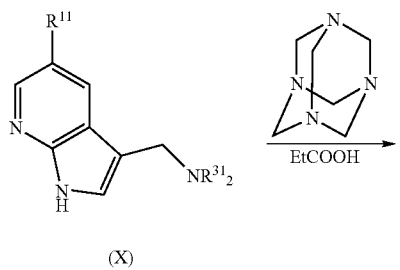

(X)

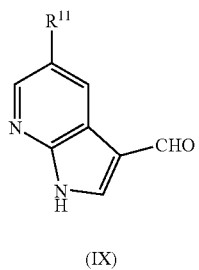

(IX)

wherein $R^{11}$ is as defined in the tenth aspect, and $R^{31}$ is as defined in the fifth aspect of the invention.

A compound of formula (IX) may undergo one or more further reactions to provide a different compound of formula (IX). For example, a compound may undergo a reduction, oxidation, elimination, substitution and/or addition reaction. In particular, a compound of formula (IX) may undergo a Stille reaction, which can be carried out according to Stille (*Angew. Chem., Int. ed, Engl.* 1986, 25, 508; Mitchell *Synthesis,* 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020).

The seventeenth aspect of the invention provides a compound of formula (X)

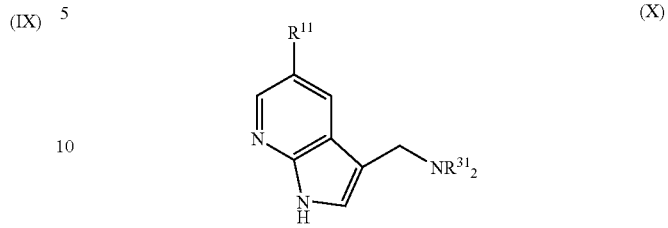

(X)

wherein $R^{11}$ is as defined in the tenth aspect, and wherein $R^{31}$ is as defined in the fifth aspect of the invention.

The eighteenth aspect of the invention provides a process for the manufacture of a compound of formula (X) as defined in the seventeenth aspect of the invention by the reaction of a compound of a formula (IX) with a secondary amine and paraformaldehyde.

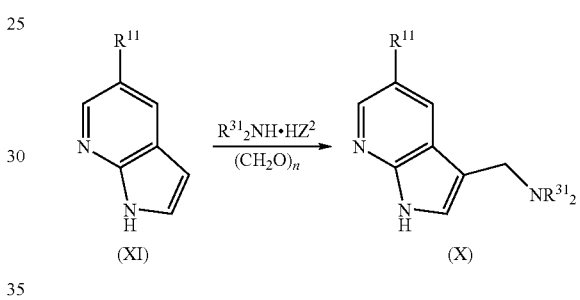

(XI)      (X)

wherein $R^{11}$ is as defined in the tenth aspect, wherein $R^{31}$ is as defined is as defined in the fifth aspect of the invention and $HZ^2$ is HCl, HBr, HI, $H_2SO_4$, $HNO_3$ or $H_3PO_4$.

Preferably the formation of the compound of formula (X) is carried out under the conditions similar to those used by Robison, M. M. Robison, B. L. (*J. Am. Chem. Soc.* 1955, 77, 457).

A compound of formula (X) may undergo one or more further reactions to provide a different compound of formula (X). For example, a compound may undergo a reduction, oxidation, elimination, substitution and/or addition reaction. In particular, a compound of formula (X) may undergo a Stille reaction, which can be carried out according to Stille (*Angew. Chem., Int. ed, Engl.* 1986, 25, 508; Mitchell *Synthesis,* 1992, 803) or Littke et al. (*J. Am. Chem. Soc.* 2002, 124, 6343), or a Suzuki reaction which can be carried out according to Suzuki (*Pure Appl. Chem.* 1991, 63, 419) or Littke et al. (*J. Am. Chem. Soc.* 2000, 122, 4020).

Methods for producing a compound of formula XI, wherein $R^{11}=R^1$ are disclosed in GB0207488.8; methods of producing a compound of formula XI, wherein $R^{11}=Br$ are known in the art (Merour and Joseph *Current Org. Chem.* 2001, 5, 471).

The nineteenth aspect of the invention provides a process for the formation of a compound of formula (IV) by the palladium catalyzed introduction of the group C≡Y-Z into compound (XII).

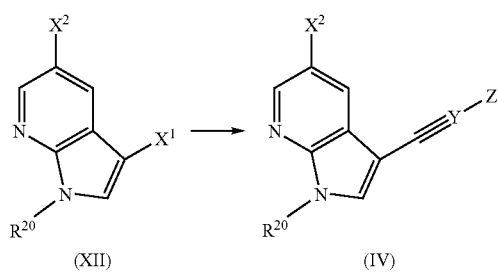

wherein Y and Z are as defined in the first aspect
wherein $R^{20}$ is as defined in the second aspect and
wherein $X^1$ is as defined in the fourth aspect
wherein $X^2$ is as defined in the fifth aspect Preferably the compound of formula (IV) can be produced from a compound of formula (XII) and acetylene H—C≡C-Z by incubation with $PdCl_2(PPh_3)_2$ and CuI.

Preferably $R^{20}$ is sulfonamide, most preferably benzenesulfonamide.

A method for producing a compound of formula (XII) is disclosed in PCT/GB2004/000944.

The present invention also encompasses a process for manufacturing a compound of the first aspect, the process comprising providing a starting material, which is commercially available or can be produced by a method known in the art, converting the starting material to form an intermediate compound of the third, seventh, ninth, eleventh, thirteenth, fifteenth or seventeenth aspects using a process as described above or a process known in the art (and optionally converting the intermediate compound so formed into another intermediate compound) and then converting the intermediate compound into a compound of the first aspect using a process as described above or a process known in the art (and optionally converting the compound of the first aspect so formed into another compound of the first aspect).

Examples of such intermediate compounds of the invention include

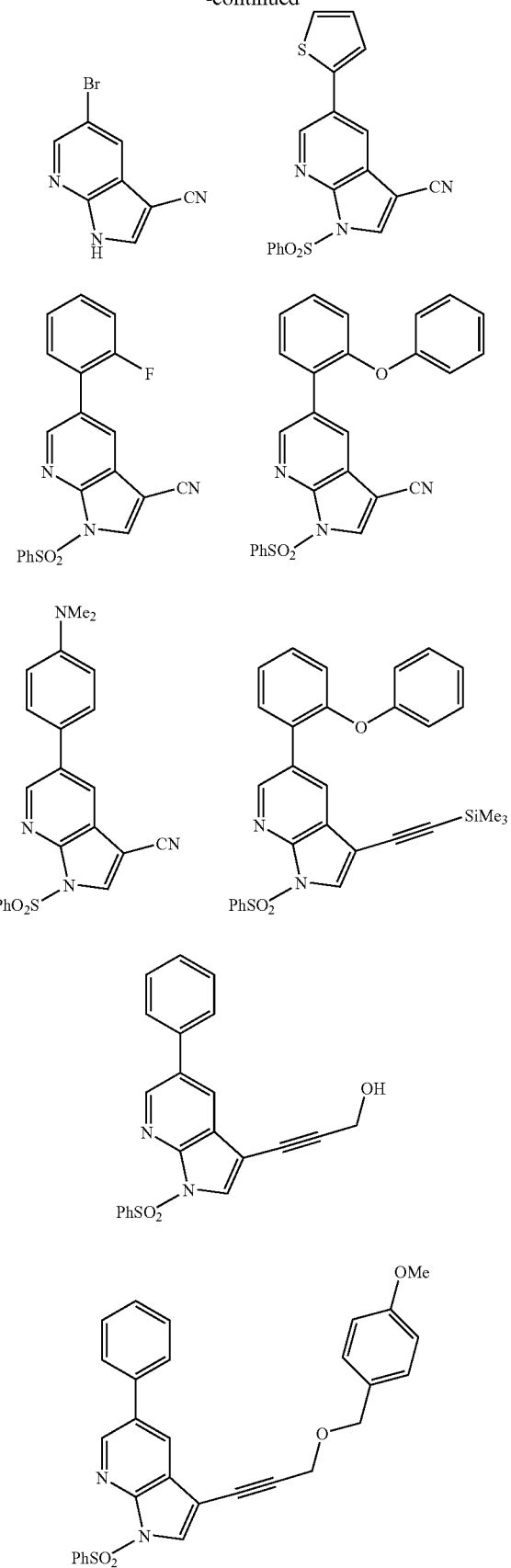

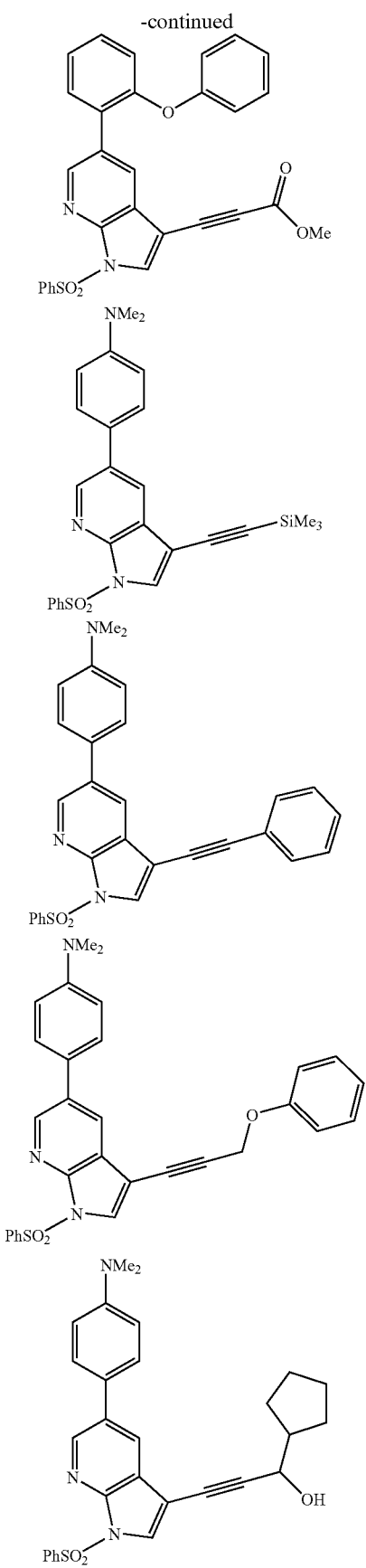
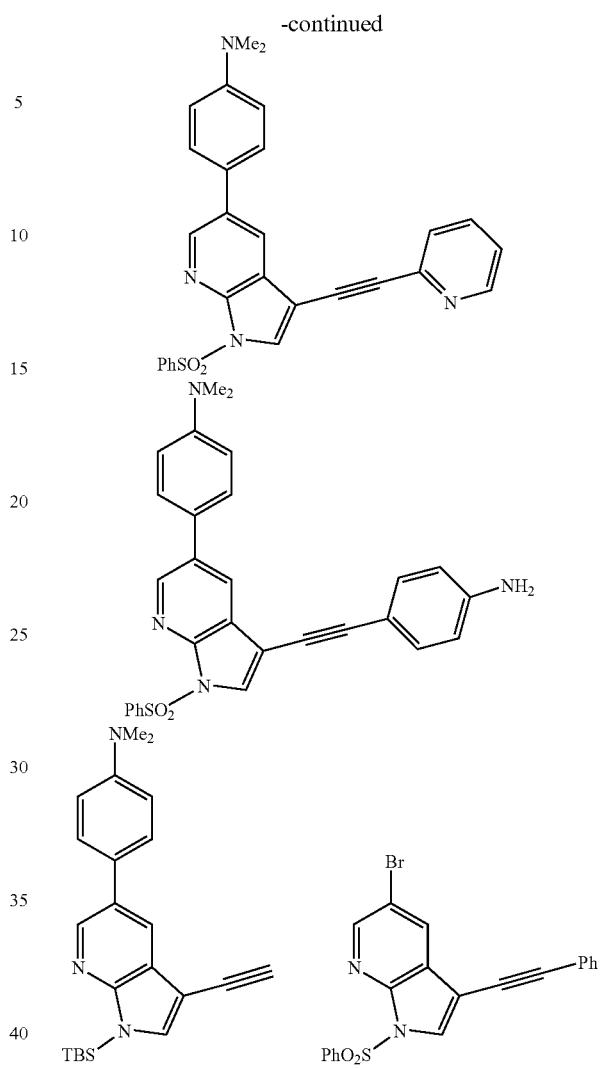

The twentieth aspect of the invention provides a composition comprising a compound according to the first aspect of the invention in combination with a pharmaceutically acceptable carrier, diluent or excipient.

The composition may also comprise one or more additional active agent, such as an anti-inflammatory agent (for example a p38 inhibitor, glutamate receptor antagonist, or a calcium channel antagonist), AMPA receptor antagonist, a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The twenty first aspect of the invention provides a process for the manufacture of a composition according to the twentieth aspect of the invention. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

The twenty-second aspect of the present invention relates to a compound of the first aspect, or a composition of the twentieth aspect, for use in medicine.

The compounds of the present invention are inhibitors of JNK, such as JNK1, JNK2, or JNK3. In particular, the compounds of the present invention are inhibitors of JNK3. Preferably, the compounds of the present invention inhibit JNK3 selectively (i.e. the compounds of the invention preferably show greater activity against JNK3 than JNK1 and 2). For the purpose of this invention, an inhibitor is any compound which reduces or prevents the activity of the JNK enzyme.

The compounds are therefore useful for conditions for which inhibition of JNK activity is beneficial. Thus, preferably, this aspect provides a compound of the first aspect, or a composition of the twentieth aspect of the present invention, for the prevention or treatment of a JNK-mediated disorder. The compounds of the first aspect of the invention may thus be used for the inhibition of JNK, more preferably for the inhibition of JNK3.

A "JNK-mediated disorder" is any disease or deleterious condition in which JNK plays a role. Examples include neurodegenerative disorder (including dementia), inflammatory disease, a disorder linked to apoptosis, particularly neuronal apoptosis, autoimmune disease, destructive bone disorder, proliferative disorder, cancer, infectious disease, allergy, ischemia reperfusion injury, heart attack, angiogenic disorder, organ hypoxia, vascular hyperplasia, cardiac hypertrophy, thrombin induced platelet aggregation and any condition associated with prostaglandin endoperoxidase synthase-2. The compounds of the present invention may be used for any of these JNK-mediated disorders.

The compounds of the present invention are particularly useful for the prevention or treatment of a neurodegenerative disorder. In particular, the neurodegenerative disorder results from apoptosis and/or inflammation.

Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The neurodegenerative disorder may be a peripheral neuropathy, including mononeuropathy, multiple mononeuropathy or polyneuropathy. Examples of peripheral neuropathy may be found in diabetes mellitus, Lyme disease or uremia; peripheral neuropathy caused by a toxic agent; demyelinating disease such as acute or chronic inflammatory polyneuropathy, leukodystrophies, or Guillain-Barré syndrome; multiple mononeuropathy secondary to a collagen vascular disorder (e.g. polyarteritis nodosa, SLE, Sjögren's syndrome); multiple mononeuropathy secondary to sarcoidosis; multiple mononeuropathy secondary to a metabolic disease (e.g. diabetes or amyloidosis); or multiple mononeuropathy secondary to an infectious disease (e.g Lyme disease or HIV infection).

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, AMPA receptor antagonist, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of,. for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The twenty-third aspect of the invention relates to a method of treating or preventing a JNK-mediated disorder in an individual, which method comprises administering to said individual a compound of the first aspect or a composition of the twentieth aspect. The active compound is preferably administered in a cumulative effective amount. The individual may be in need of the treatment or prevention. Any of the JNK-mediated disorders listed above in relation to the twenty-second aspect may be the subject of treatment or prevention according to the twenty-third aspect. One or more other active agent may be administered to the individual simultaneously, subsequently or sequentially to administering the compound. The other active agent may be an anti-inflammatory agent such as a p38 inhibitor, glutamate receptor antagonist, AMPA receptor antagonist, calcium channel antagonist, a chemotherapeutic agent or an antiproliferative agent, but is preferably p38 inhibitor for acute treatment.

The twenty-fourth aspect of the present invention provides the use of a compound of the first aspect in the manufacture of a medicament for the prevention or treatment of a JNK-mediated disorder. The medicament may be used for treatment or prevention of any of the JNK-mediated disorders listed above in relation to the twenty-second aspect. Again, the compound of the present invention may be administered simultaneously, subsequently or sequentially with one or more other active agent, preferably a p38 inhibitor for acute treatment.

In the twenty-fifth aspect of the invention, there is provided an assay for determining the activity of the compounds of the present invention. Preferably the assay is for the JNK inhibiting activity of the compound, more preferably it is for the JNK3-specific inhibiting activity of the compounds. The compounds of the invention may be assayed in vitro, in vivo, in silico, or in a primary cell culture or a cell line. In vitro assays include assays that determine inhibition of either the kinase activity or ATPase activity of activated JNK. Alternatively, in vitro assays may quantitate the ability of a compound to bind JNK and may be measured either by radiolabelling the compound prior to binding, then-isolating the inhibitor/JNK complex and determining the amount of the radiolabel bound or by running a competition experiment where new inhibitors are incubated with JNK bound to known radioligands. An example of an assay, which may be used, is Scintillation Proximity Assay (SPA), preferably using radio-labelled ATP. Another example is ELISA. Any type or isoform of JNK may be used in these assays.

In the twenty-sixth aspect, there is provided a method of inhibiting the activity or function of a JNK, particularly JNK3, which method comprises exposing a JNK to a compound or a composition of the first or twentieth aspect of the present invention. The method may be performed in a research model, in vitro, in silico, or in vivo such as in an animal model. A suitable animal model may be a kainic acid model in rat or mice, traumatic brain injury model in rat, or MPTP in mice.

All features of each of the aspects apply to all other aspects *mutatis mutandis*.

The invention will now be illustrated by the following non-limiting examples.

EXAMPLES

Synthesis of Example Inhibitor 3

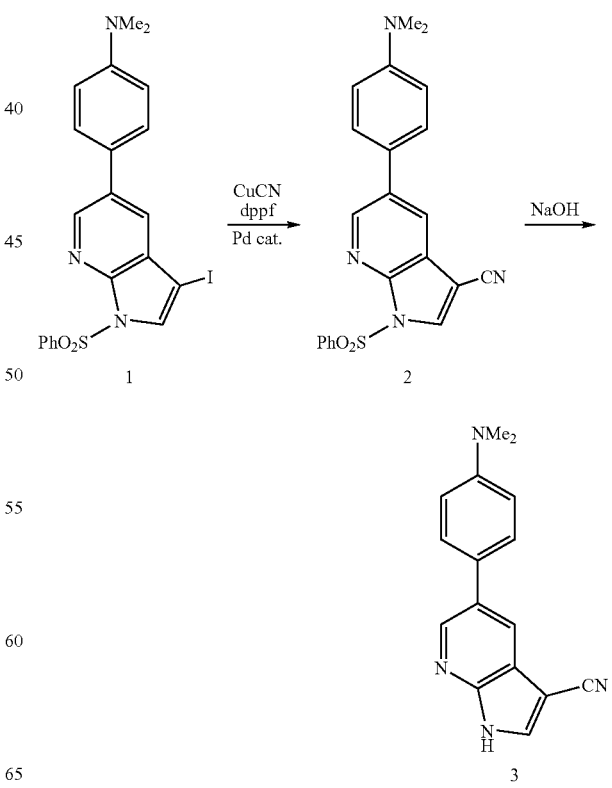

1-Benzenesulfonyl-5-(4-dimethylamino-phenyl)-1H-pyrrolo[2,3-b]pyridine-3-carbonitrile (2)

5-(4-Dimethylamino-phenyl)-1H-pyrrolo[2,3-b]pyridine-3-carbonitrile (3)

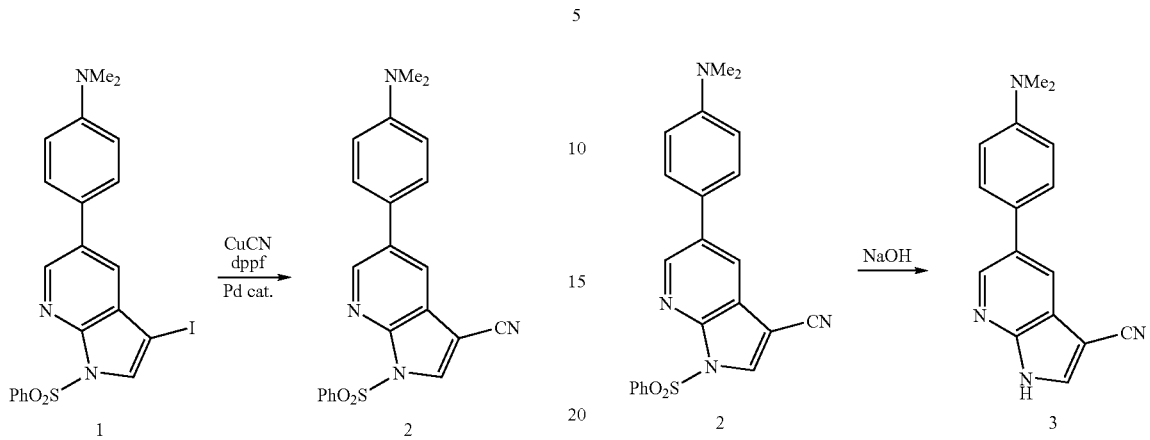

A mixture of 1 (80.0 mg, 0.159 mmol; prepared as described in GB0305144.8), CuCN (57.0 mg, 0.636 mmol), Pd$_2$(DBA)$_3$ (36.0 mg, 0.0397 mmol) and dppf (14.0 mg, 0.0254 mmol) in dioxane (1.0 mL) was microwaved for 30 min at 100° C. The reaction mixture was then purified by silicagel chromatography (SGC) using 15% ethyl acetate in hexane as eluent (gradient elution) to give 2 as an orange solid (41.5 mg, 65%); $^1$H NMR (400 MHz, CDCl$_3$) δ 3.02 (s, 6H), 6.81 (d, J=8.7 Hz, 2H), 7.47 (d, J=8.7 Hz, 2H), 7.56 (t, J=7.7 Hz, 2H), 7.66 (t, J=7.4 Hz, 1H), 8.09 (t, J=2.0 Hz, 1H), 8.25 (s, 1H), 8.29 (d, J=7.7 Hz, 2H), 8.74 (d, J=2.0 Hz, 1H).

A mixture of 2 (41.5 mg, 0.103 mmol) and 10% aqueous NaOH (2.0 mL) in EtOH (4.0 mL) was heated at 110° C. for 40 min. It was then poured onto water (5 mL), extracted with ethyl acetate (4×10 mL) and the combined organic extracts dried (MgSO$_4$) and concentrated. The residue was purified by preparative TLC (PTLC) using 5% ethyl acetate in dichloromethane as eluent to give 3 as a light orange solid (14.9 mg, 36%); $^1$H NMR (400 MHz, CDCl$_3$) δ 3.06 (s, 6H), 6.86 (d, J=8.9 Hz, 2H), 7.55 (d, J=8.9 Hz, 2H), 7.89 (s, 1H), 8.25 (d, J=2.0 Hz, 1H), 8.64 (bs, 1H); MS (CI) m/z 304.0 (MH+ MeCN).

Synthesis of Example Inhibitors 9, 10, and 12

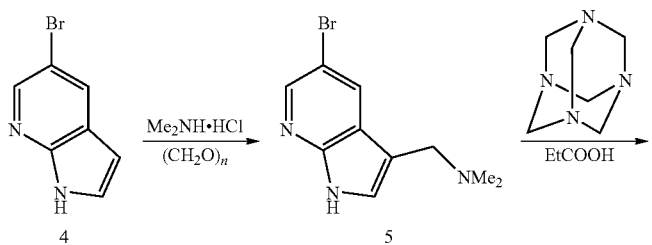

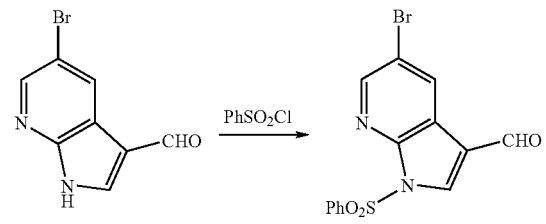

1. NH$_2$OH
2. SeO$_2$

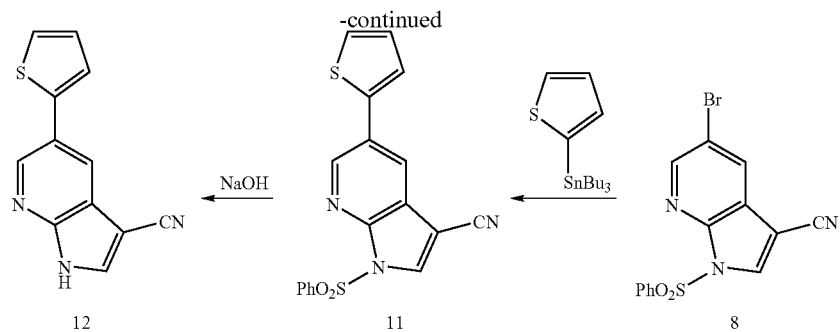

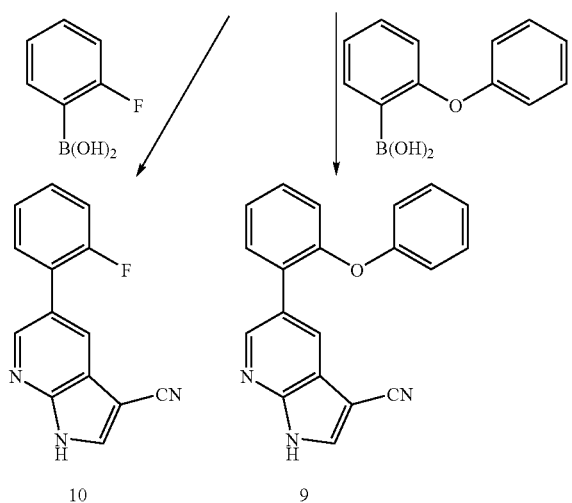

(5-Bromo-1H-pyrrolo[2,3-b]pyridin-3-ylmethyl)-dimethyl-amine (5)

5-Bromo-1H-pyrrolo[2,3-b]pyridine-3-carbaldehyde (6)

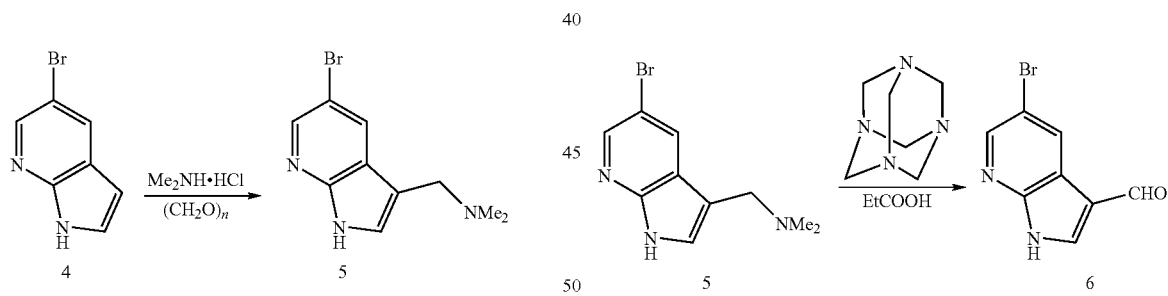

A mixture of 5-bromoazaindole 4 (20.0 g, 102 mmol), n-butanol (400 mL), ME$_2$NH·HCl (8.94 g, 110 mmol) and paraformaldehyde (3.40 g) were refluxed (125° C. oil bath) for 40 min, then evaporated to dryness. To the solid residue was added water (200 mL) then conc. HCl (16 mL) dropwise. Ether was added (150 mL) and the mixture stirred then filtered to remove any undissolved solid. The layers were separated, the aqueous layer extracted with more ether (2×150 mL) and basified with solid K$_2$CO$_3$ to pH 12. The mixture was cooled in an ice-bath and the solid filtered off and washed successively with ice-cold water (3×) and ice-cold ether (3×). Overnight drying under high vacuum gave 5 as a creamy white solid (16.53 g, 64%); $^1$H NMR (400 MHz, CDCl$_3$+4 drops d$_4$-MeOH), δ 8.22 (d, J=2.2 Hz, 1H), 8.11 (d, J=2.2 Hz, 1H), 7.23 (s, 1H), 3.45 (s, 2H), 2.21 (s, 6H).

To a refluxing (oil bath temp. 140° C.) solution of hexamethylenetetramine (8.83 g, 63 mmol) in 66% aqueous propionic acid (31.5 mL) was added a mixture of 5 (16.0 g, 63 mmol) and hexamethylenetetramine (8.83 g, 63 mmol) in 66% propionic acid (47 mL) over 2.5 h. The reflux was continued for 2.5 h, the reaction mixture allowed to cool to room temperature, then poured onto water (220 mL) and the suspension cooled in an ice-bath. The solid was filtered off, washed with ice-cold water (2×), and dried under high vacuum overnight to give 6 as a white solid (11.47 g, 81%); $^1$H NMR (400 MHz, CDCl$_3$+4 drops d$_4$-MeOH) δ 9.91 (s, 1H), 8.69 (d, J=2.2 Hz, 1H), 8.36 (d, J=2.2 Hz, 1H), 7.95 (s, 1H).

1-Benzenesulfonyl-5-bromo-1H-pyrrolo[2,3-b]pyridine-3-carbaldehyde (7)

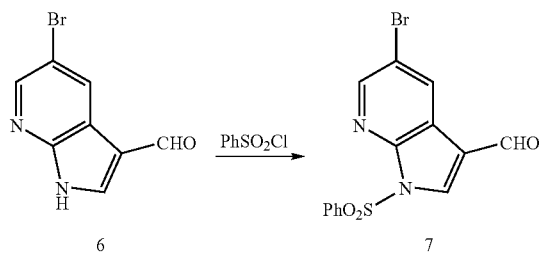

To a suspension of 6 (5.0 g, 22.2 mmol) in dichloromethane (130 mL) was added benzenesulfonyl chloride (4.25 mL, 33.3 mmol), tetra-n-butylammonium hydrogen sulphate (0.98 g, 2.98 mmol) and 50% aqueous NaOH (4.2 mL). The reaction mixture was stirred for 2 h then poured onto water (500 mL), extracted with dichloromethane (3×200 mL). The combined organic extracts were washed with saturated aqueous $NaHCO_3$ (2×150 mL) and dried ($MgSO_4$). Concentration produced a white solid which was washed with ether (3×150 mL) to give product 7 as a light orange solid (7.34 g, 91%); $^1$H NMR (400 MHz, $CDCl_3$+4 drops $d_4$-MeOH) δ 9.95 (s, 1H), 8.61 (d, J=2.3 Hz, 1H), 8.46 (d, J=2.1 Hz, 1H), 8.38 (s, 1H), 8.19 (m, 2H), 7.62 (tt, J=7.5, 1.3 Hz, 1H), 7.51 (t, J=7.1 Hz, 2H).

1-Benzenesulfonyl-5-bromo-1H-pyrrolo[2,3-b]pyridine-3-carbonitrile (8)

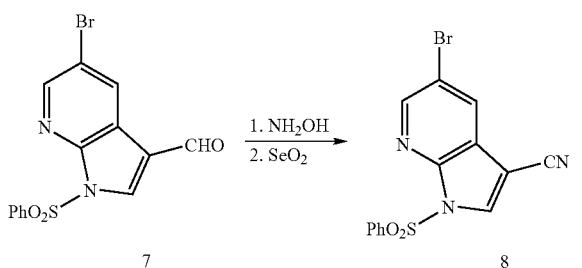

To a refluxing mixture of 7 (6.00 g, 16.4 mmol), $CHCl_3$ (30 mL), EtOH (12 mL) and $NH_2OH\cdot HCl$ (2.28 g, 32.9 mmol) was added dropwise a solution of pyridine (2.66 mL, 32.9 mmol) in $CHCl_3$ (9 mL). When the addition was complete, a Soxhlet extractor containing $MgSO_4$ was attached and the refluxing continued for 6 h. Selenium dioxide (2.73 g, 24.6 mmol) was then added portionwise over 1 h during reflux. Each time selenium dioxide was added an exothermic reaction occurred. When the addition was complete the reaction mixture was heated at reflux overnight. More $SeO_2$ (1.00 g, 9.0 mmol) was added in one portion and the reflux continued for a further 1.5 h. The reaction mixture was cooled, sorbent (HM-N, Jones chromatography) added and the solvent evaporated. Purification by means of SGC using dichloromethane:hexane (1:1) (gradient elution) gave the product 8 (3.80 g, 64%) as a white solid; $^1$H NMR (400 MHz, $CDCl_3$) δ 8.56 (d, J=2.2 Hz, 1H), 8.22 (m, 3H), 8.16 (d, J=2.1 Hz, 1H), 7.68 (tt, J=7.5, 1.2 Hz, 1H), 7.56 (t, 7.5 Hz, 2H).

5-(2-Phenoxy-phenyl)-1H-pyrrolo[2,3-b]pyridine-3-carbonitrile (9)

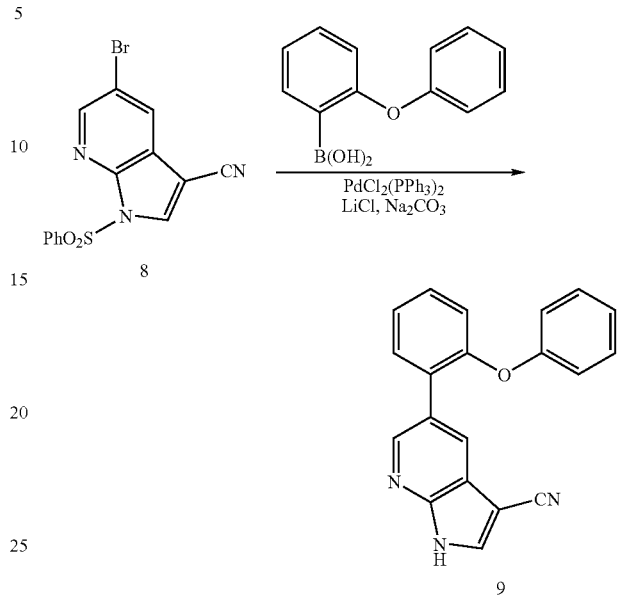

A mixture of 8 (40.0 mg, 0.11 mmol), 2-phenoxyphenylboronic acid (35.5 mg, 0.166 mmol), $PdCl_2(PPh_3)_2$ (7.8 mg, 0.011 mmol), LiCl (14.0 mg, 0.33 mmol), 1M $Na_2CO_3$ (276 µL, 0.28 mmol) in EtOH (0.66 mL) and toluene (0.66 mL) was heated at 105° C. for 0.5 h in a sealed reaction tube. Reaction mixture was separated between ethyl acetate and brine. The aqueous layer was extracted with ethyl acetate (2×). The combined organic solutions were concentrated and purified by PTLC using ethyl acetate:hexane (1:1) as eluent to give 9 as a white solid (13.8 mg, 40%); $^1$H NMR (400 MHz, $CDCl_3$) δ 12.80-12.60 (bs, NH), 8.69 (d, J=2.0 Hz, 1H), 8.34 (d, J=2.0 Hz, 1H), 7.87 (s, 1H), 7.53 (dd, J=7.6, 1.7 Hz, 1H), 7.40 (dt, J=7.5, 1.8 Hz, 1H), 7.29 (m, 3H), 7.06 (m, 2H), 6.94 (m, 2H); MS (CI) m/z 352.8 (MH+MeCN).

5-(2-Fluoro-phenyl)-1H-pyrrolo[2,3-b]pyridine-3-carbonitrile (10)

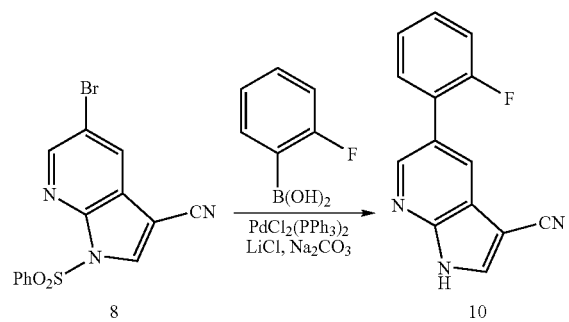

Compound 10 was synthesized according to the procedure used for the preparation of 9 using 8 (40.0 mg, 0.11 mmol), 2-fluorophenylboronic acid (23.2 mg, 0.11 mmol), $PdCl_2(PPh_3)_2$ (7.8 mg, 0.011 mmol), LiCl (14.0 mg, 0.33 mmol), 1M $Na_2CO_3$ (276 mL), EtOH (0.66 mL) and toluene (0.66 mL) with refluxing for 1 h. Obtained 10 (9.9 mg, 38%) as a white solid; $^1$H NMR (400 MHz, CDCl$_3$+4 drops d$_4$-MeOH) δ 8.54 (t, J=1.9 Hz, 1H), 8.25 (dd, J=2.0, 1.3 Hz, 1H), 7.89 (s, 1H), 7.46 (dt, J=7.7, 1.8 Hz, 1H), 7.37 (m, 1H), 7.30-7.10 (m, 2H).

1-Benzenesulfonyl-5-thiophen-2-yl-1H-pyrrolo[2,3-b]pyridine-3-carbonitrile (11)

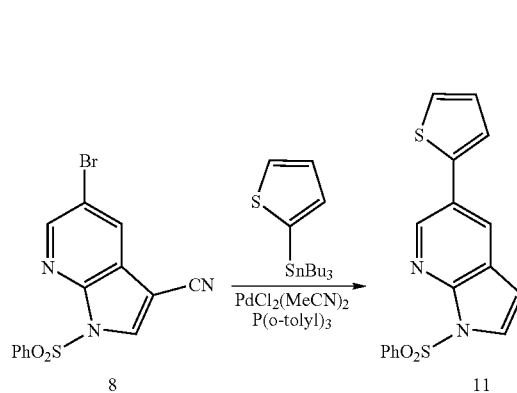

A mixture of 8 (50.0 mg, 0.128 mmol), 2-(tributylstannyl)thiophene (88 μL, 0.276 mmol), dichlorobis(acetonitrile)palladium (II) (4.0 mg, 0.0138 mmol), tri-o-tolylphosphine (8.0 mg, 0.0276 mmol) and toluene (1.0 mL) were heated at 90° C. overnight. The mixture was separated by PTLC using ethyl acetate:hexane (3:7) as eluent to give 11 as a white solid (18.3 mg, 36%); $^1$H NMR (400 MHz, CDCl$_3$) δ 8.80 (d, J=2.1 Hz, 1H), 8.28 (m, 3H), 8.16 (d, J=2.1 Hz, 1H), 7.68 (tt, J=7.5, 1.2 Hz, 1H), 7.57 (t, J=4.1 Hz, 2H), 7.37 (m, 2H), 7.13 (dd, J=5.1, 3.6 Hz, 1H).

5-Thiophen-2-yl-1H-pyrrolo[2,3-b]pyridine-3-carbonitriie (12)

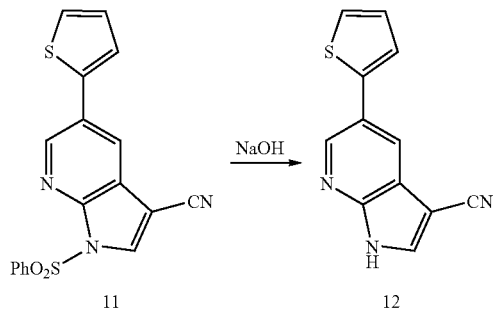

A mixture of 11 (18.3 mg, 50.1 μmol), EtOH (2.0 mL) and 10% aqueous NaOH (1.0 mL) was refluxed (oil bath temp. 105° C.) for 40 min. The mixture was poured onto water (3 mL), extracted with ethyl acetate (3×10 mL). The combined organic extracts were dried (MgSO$_4$) and concentrated. The product was isolated by PTLC using dichloromethane:methanol (19:1) as eluent to give 12 as a white solid (7.6 mg, 68%); $^1$H NMR (400 MHz, CDCl$_3$) δ 10.30-10.10 (bs, NH), 10.74 (d, J=1.9 Hz, 1H), 8.31 (d, J=1.9 Hz, 1H), 7.90 (s, 1H), 7.39 (m, 2H), 7.16 (dd, J=5.0, 3.6 Hz, 1H).

Synthesis of Example Inhibitor 16

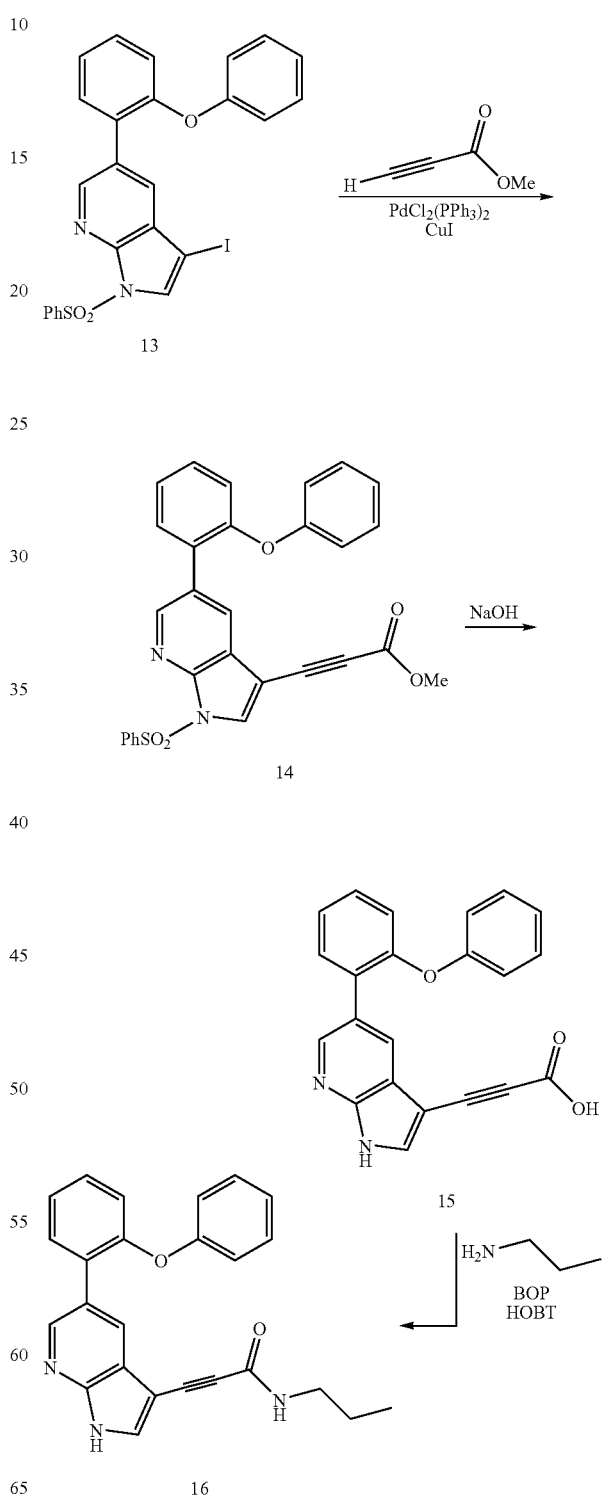

[1-Benzenesulfonyl-5-(2-phenoxy-phenyl)-1H-pyrrolo[2,3-b]pyridin-3-yl]-propynoic acid methyl ester (14)

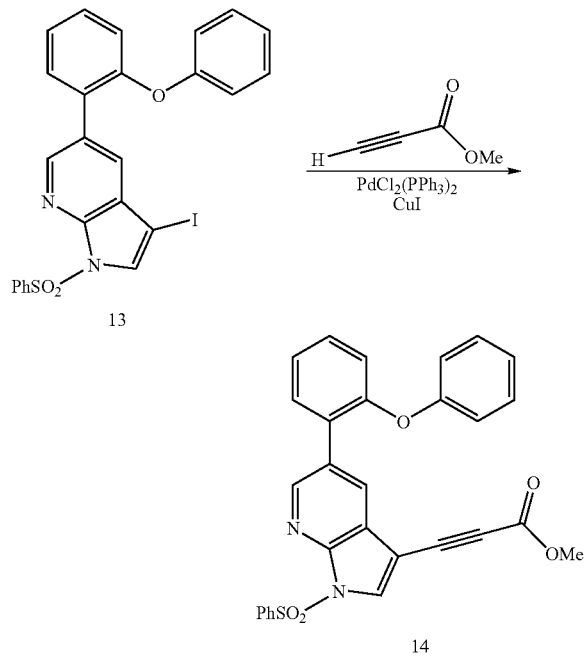

A mixture of iodide 13 (100 mg, 0.181 mmol), methyl propiolate (32 μL, 0.362 mmol), PdCl$_2$(PPh$_3$)$_2$ (12.7 mg, 0.0181 mmol), CuI (5.9 mg, 0.0308 mmol) in Et$_3$N (3.14 mL) was heated at 70° C. overnight. TLC showed presence of starting material so more methyl propiolate (32 μL, 0.362), PdCl$_2$(PPh$_3$), (12.7 mg, 0.0181) and CuI (5.9 mg, 0.0308 mmol) were added and the reaction mixture heated at 80° C. for 2.5 h. The solution was decanted off and the solid washed with more Et$_3$N. The combined solutions were concentrated. The residue was purified by PTLC (3×1 mm plates, 30% ethyl acetate in hexane) to give 14 as an orange solid (35 mg, 38%); $^1$H NMR (400 MHz, CDCl$_3$) δ 3.77 (s, 3H), 6.82 (m, 2H), 6.93 (m, 2H), 7.18 (m, 2H), 7.27 (dt, J=8.1, 1.7 Hz, 1H), 7.36 (dd, J=8.1, 1.7 Hz, 1H), 7.40-7.60 (m, 4H), 8.04 (s, 1H), 8.08 (d, J=2.1 Hz, 1H), 8.15 (m, 2H), 8.64 (d, J=2.0 Hz, 1H).

[5-(2-Phenoxy-phenyl)-1H-pyrrolo[2,3-b]pyridin-3-yl]-propynoic acid (15)

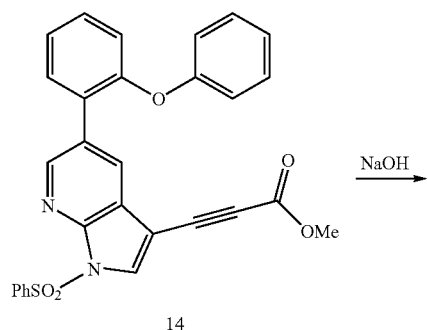

A mixture of ester 14 (30 mg, 0.059 mmol), EtOH (593 μL) and 10% aq. NaOH (296 μL) was heated at 90° C. for 1 h. The reaction mixture was cooled, concentrated and acidified to pH 5 with 1N HCl. The mixture was then extracted with ethyl acetate (4×10 mL). The combined organic extracts were dried (MgSO$_4$) and concentrated to give the crude product 15 (23 mg, 110%) which was used for the subsequent reactions without further purification.

3-[5-(2-Phenoxy-phenyl)-1H-pyrrolo[2,3-b]pyridin-3-yl]-propynoic acid propylamide (4)

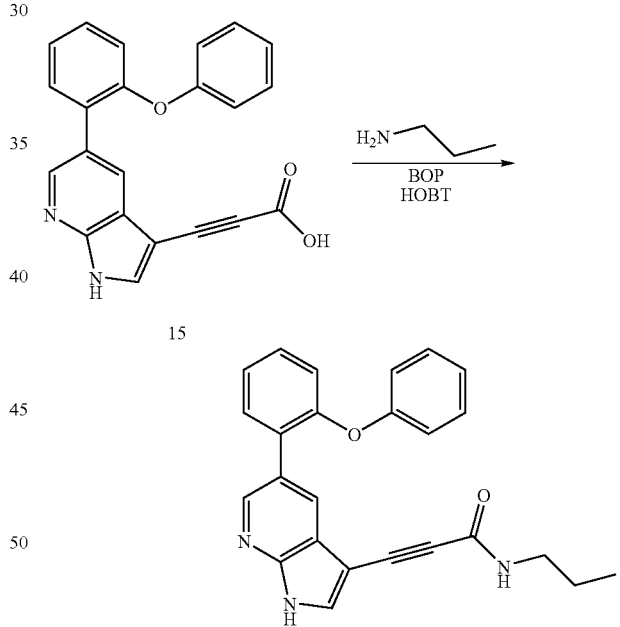

A mixture of acid 15 (21 mg, 0.0593 mmol), n-PrNH$_2$ (7.0 mg, 0.119 mmol), HOBt (12.0 mg, 0.089 mmol), BOP (34.0 mg, 0.077 mmol), N-ethyldiisopropylamine (15.0 mg, 0.119 mmol) in DMF (1.0 mL) was stirred for 2 h then purified by preparative LCMS (column LUNA 10μ C18(2) 00G4253-V0 250×50 mm) using water-acetonitrile (0.1% AcOH) as eluent (in gradient; flow 80 mL/min) to give pure product 16 (4.0 mg, 17%) as a white solid; $^1$H NMR (400 MHz, CDCl$_3$) δ 0.80 (t, J=7.4 Hz, 3H), 1.42 (sextet, J=7.3 Hz, 2H), 3.15 (q, J=7.7 Hz, 2H), 5.67 (t, J=5.8 Hz, NH), 6.74 (d, J=7.7 Hz, 2H), 6.82 (m, 1H), 6.88 (dd, J=8.1, 1.1 Hz, 1H), 7.08 (m, 3H), 7.18

(dt, J=9.2, 1.7 Hz, 1H), 7.34 (dd, J=7.7, 1.8 Hz, 1H), 7.54 (s, 1H), 8.03 (s, 1H), 8.41 (bs, 1H), 10.52 (bs, NH).

[4-(3-Ethynyl-1H-pyrrolo[2,3-b]pyridin-5-yl)-phenyl]-dimethyl-amine (18)

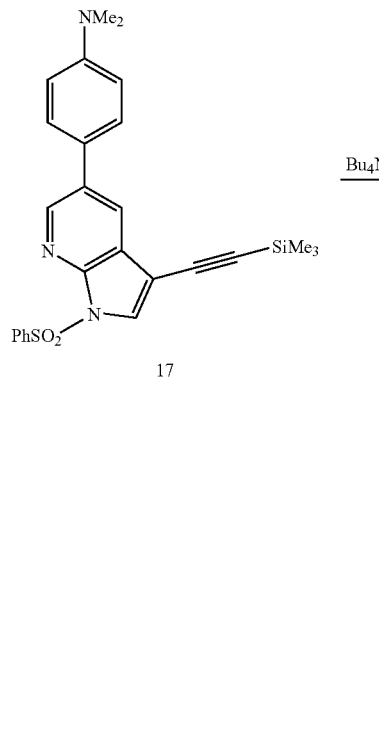

To a solution of 17 (140 mg, 0.296 mmol; prepared in an analogous way to 14) in THF (13.0 mL) was added 1.0 M tetrabutylammonium fluoride in THF (591 μL, 0.591 mmol), and the reaction mixture was stirred for 1.5 h. It was then portioned between brine and ethyl acetate and the aqueous layer extracted with more ethyl acetate (3×30 mL). The combined organic solutions were dried (MgSO$_4$) and concentrated. The residue was purified by silicagel chromatography using ethyl acetate:hexane (7:3, gradient elution) to give 18 as a light green solid (58 mg, 75%); $^1$H NMR (400 MHz, CDCl$_3$+6 drops d$_4$-MeOH) δ 2.94 (s, 6H), 3.17 (s, 1H), 6.79 (d, J=8.8 Hz, 2H), 7.47 (d, J=8.8 Hz, 2H), 7.50 (s, 1H), 8.12 (d, J=1.9 Hz, 1H), 8.41 (bs, 1H).

Synthesis of Example Inhibitor 22

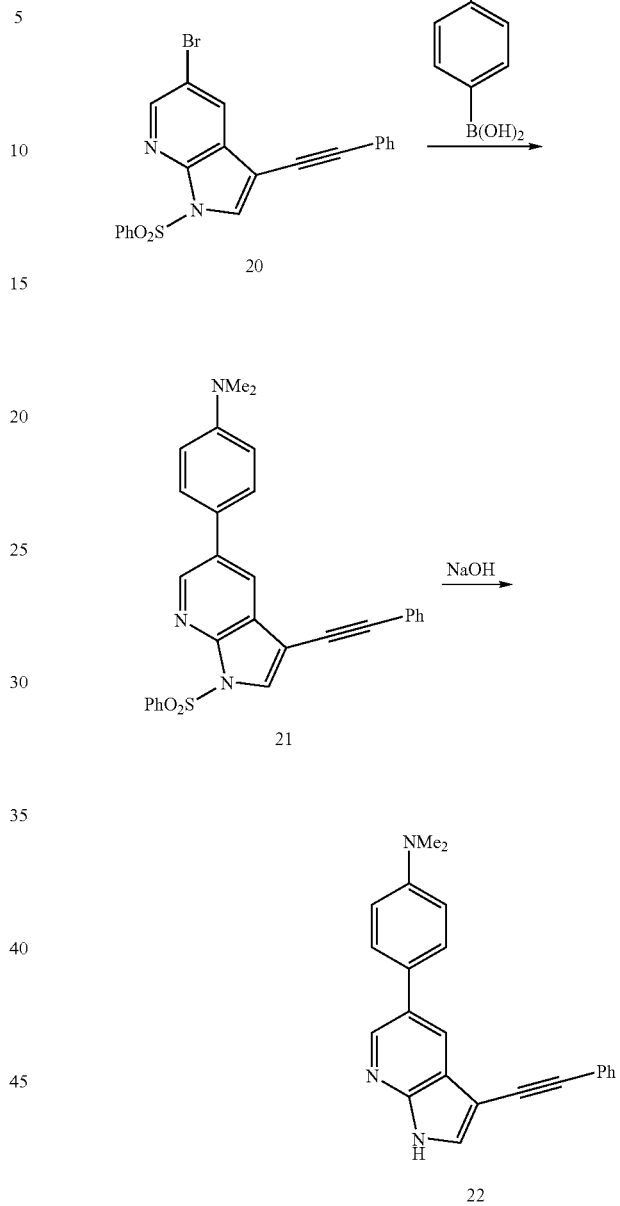

1-Benzenesulfonyl-5-bromo-3-phenylethynyl-1H-pyrrolo[2,3-b]pyridine (20)

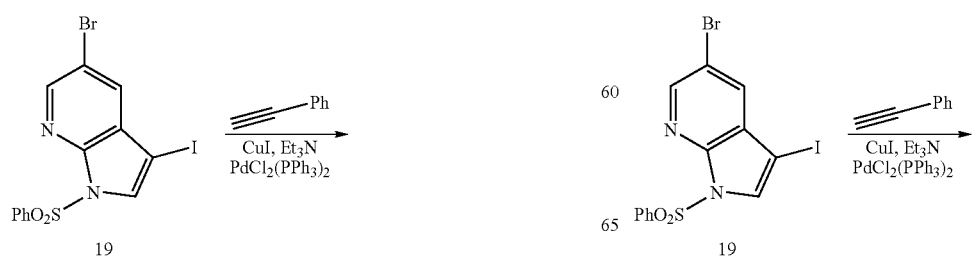

-continued

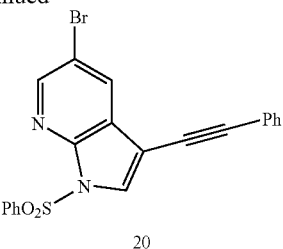

20

A mixture of iodide 19 (300 mg, 0.647 mmol; preparation disclosed in PCT/GB2004/000944), PdCl$_2$(PPh$_3$)$_2$ (45 mg, 0.064 mmol), CuI (21 mg, 0.110 mmol) and phenylacetylene (142 μL, 1.295 mmol) in Et$_3$N (11.2 mL) was stirred for 1 h at 80° C. The reaction mixture was then evaporated to dryness and purified by preparative LCMS (column LUNA 10μ C18 (2) 00G-4253-V0 250×50 mm) using water-acetonitrile (0.1% AcOH) as eluent (in gradient; flow 80 mL/min) to give the product 20 as a yellow solid (53 mg, 19%); $^1$H NMR (400 MHz, CDCl$_3$) δ 7.33-7.39 (m, 3H), 7.52-7.62 (m, 5H), 7.96 (s, 1H), 8.14 (d, J=2.18 Hz, 1H), 8.16-8.21 (m, 2H), 8.50 (d, J=2.17 Hz, 1H).

[4-(1-Benzenesulfonyl-3-phenylethynyl-1H-pyrrolo[2,3-b]pyridin-5-yl)-phenyl]-dimethyl-amine (21)

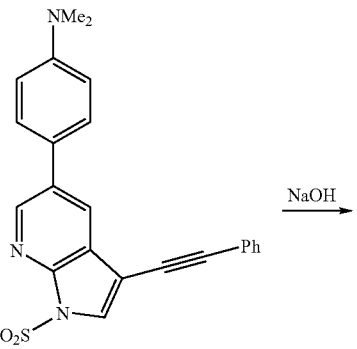

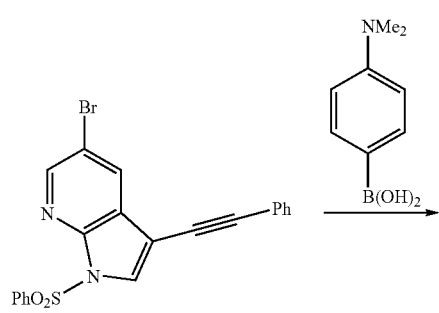

21

A mixture of acetylene 20 (53 mg, 0.121 mmol), 4-(N,N-dimethylamino)phenylboronic acid (30 mg, 0.182 mmol), PdCl$_2$(PPh$_3$)$_2$ (9.0 mg, 0.012 mmol), LiCl (15 mg, 0.363 mmol) and 1.0 M aq. Na$_2$CO$_3$ (300 μL, 0.302 mmol) in EtOH (2 mL) and toluene (2 mL) was stirred for 2 h 45 min. at 105° C. The reaction mixture was then poured onto brine (5 mL) and extracted with ethyl acetate (4×10 mL) and the combined organic extracts dried (MgSO$_4$) and concentrated. The residue was purified by preparative LCMS (column LUNA 10μ C18(2) 00G-4253-V0 250×50 mm) using water-acetonitrile (0.1% AcOH) as eluent (in gradient; flow 80 mL/min) to give product 21 as a yellow solid (36.85 mg, 64%); $^1$H NMR (400 MHz, CDCl$_3$) δ 3.01 (s, 6H), 6.82 (d, J=8.82 Hz, 2H), 7.35-7.42 (m, 3H), 7.45-7.65 (m, 7H), 7.95 (s, 1H), 8.08 (d, J=2.14 Hz, 1H), 8.23 (m, 2H), 8.68 (d, J=2.13 Hz, 1H).

Dimethyl-[4-(3-phenylethynyl-1H-pyrrolo[2,3-b]pyridin-5-yl)-phenyl]-amine (22)

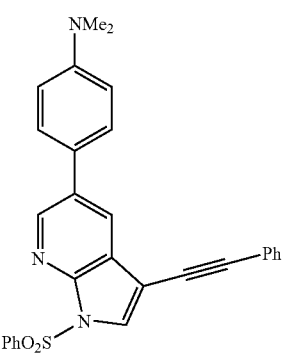

To sulfonamide 21 (36.9 mg, 0.077 mmol) in EtOH (770 μL) was added 10% aq. NaOH (386 μL) and the reaction mixture heated at 90° C. for 1 h. It was then poured onto water (5 mL), extracted with ethyl acetate (4×10 mL) and the combined organic extracts dried (MgSO$_4$) and concentrated. The residue was purified by preparative LCMS (column LUNA 10μ C18(2) 00G4253-V0 250×50 mm) using water-acetonitrile (0.1% AcOH) as eluent (in gradient; flow 80 mL/min) to give inhibitor 22 as a white solid (7.3 mg, 28%); $^1$H NMR (400 MHz, CDCl$_3$) δ 6.86 (d, J=8.85 Hz, 2H), 7.31-7.39 (m, 3H), 7.57-7.62 (m, 5H), 8.24 (d, J=1.87 Hz, 1H), 8.59 (d, J=1.80 Hz, 1H), 9.83 (bs, 1H).

Biological Activity

JNK1, JNK2, JNK3—SPA Assay
1. Compound is dissolved in DMSO to a convenient concentration and this is diluted in 10% DMSO to a five times concentrate of the desired starting concentration (frequently 1:100).
2. 10 μl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.

4. 20 μl per well of each compound concentration is transferred to an Opti-plate, in duplicate.
5. 30 μl (JNK2/3 SPA) or 50 μl (JNK1 SPA) of substrate solution (25 mM HEPES pH 7.5, 10 mM magnesium acetate with 3.33 μM ATP (JNK2/3) or 2 μM ATP (JNK1), approximately 7.5 kBq [γ-$^{33}$P] ATP, GST-c-Jun, in water) is added to each well.
6. 50 μl (JNK2/3 SPA) or 30 μl (JNK1 SPA) of kinase solution (JNK in 25 mM HEPES pH 7.5, 10 mM Mg Acetate) is added to each well.

| Kinase | Kinase per well (μg) | GST-c-Jun per well (μg) |
| --- | --- | --- |
| JNK1 | 0.25 | 1 |
| JNK2 | 0.2 | 1.2 |
| JNK3 | 0.16 | 1.2 |

7. The plate is incubated for 30 minutes at room temperature.
8. 100 μl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The $IC_{50}$ values are calculated as the concentration of the compound being tested at which the phosphorylation of c-Jun is decreased to 50% of the control value. Example $IC_{50}$ values for the compounds of this invention are given in Table 1.

p38 ELISA

Active p38 kinase (100 ng; Upstate) was added to 2 μg GST-ATF2 substrate (NEB) in 250 mM Hepes pH 7.5/100 mM MgAc/50 μM ATP (final) in the presence or absence of compounds in 50 μl. The mixture was incubated at 30° C. for 1 hour, and then diluted with 200 μl PBS-Tween (0.05%). From this, duplicate volumes of 100 μl were added to a Reacti-Bind glutathione coated plate (Pierce) and incubated for 1 hour. After washing 3 times with PBS-Tween (0.05%), rabbit anti-phospho-ATF2 (Thr71) antibody (NEB) was added at 1:500, and incubated for another hour at room temperature. After 3 additional washes with PBS-Tween (0.05%), 100 μl of anti-rabbit IgG alkaline phosphatase-conjugated secondary antibody (Sigma) was added at 1:1000, the reaction was incubated for a further hour, washed 3 times, and then phosphatase substrate (Sigma) was added (100 μl per well; 3 tablets in 5 ml water). After incubation in the dark at 37° C. for 1 hour, the reaction mixture was transferred to a clear 96 well plate, and the absorbance at 405 nm was read. The $IC_{50}$ values are calculated as the concentration of the compound being tested at which the phosphorylation of ATF2 is decreased to 50% of the control value. Example $IC_{50}$ values for the compounds of this invention are given in Table 1 (last column).

TABLE 1

$IC_{50}$ values for selected compounds against JNK3 kinase

| Compound | JNK3 $IC_{50}$ (nM) |
| --- | --- |
| | <500 |
| | <500 |
| | <500 |
| | <500 |

The invention claimed is:

1. A compound of formula (I) or a pharmaceutically acceptable salt thereof

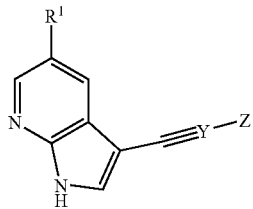

(I)

wherein $R^1$ is an optionally substituted $C_{3-12}$ carbocyclyl or $C_{3-12}$ heterocyclyl group, Y is N or C and Z is lone electron pair, hydrogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $(CH_2)_nOR^2$, $(CH_2)_nNR^2{}_2$, $CO_2R^2$, $COR^2$, $CONR^2{}_2$, wherein the $C_{1-12}$ alkyl group optionally contains one or more insertions selected from —O—, —N($R^2$)—S—, —S(O)— and —S(O$_2$)—; and each substitutable nitrogen atom in Z is optionally substituted by $R^3$, $COR^3$, $SO_2R^3$ or $CO_2R^3$;

wherein n is 1 to 6, preferably n is 1, 2 or 3;

wherein $R^2$ is hydrogen, $C_{1-12}$ alkyl, $C_{3-12}$ carbocyclyl, $C_{3-12}$ heterocyclyl, $C_{1-12}$alkyl$C_{3-12}$carbocyclyl or $C_{1-12}$alkyl$C_{3-12}$heterocyclyl optionally substituted by one or more of $C_{1-6}$ alkyl, halogen, $C_{1-6}$ haloalkyl, $OR^4$, $SR^4$, $NO_2$, CN, $NR^4R^4$, $NR^4COR^4$, $NR^4CONR^4R^4$, $NR^4COR^4$, $NR^4CO_2R^4$, $CO_2R^4$, $COR^4$, $CONR^4{}_2$, $S(O)_2R^4$, $SONR^4{}_2$, $S(O)R^4$, $SO_2NR^4R^4$, $NR^4S(O)_2R^4$, wherein the $C_{1-12}$ alkyl group optionally incorporates one or two insertions selected from the group consisting of —O—, —N($R^4$)—, —S(O)— and —S(O$_2$)—, wherein each $R^4$ may be the same or different and is as defined below;

wherein two $R^2$ in $NR^2{}_2$ may form a partially saturated, unsaturated or fully saturated five to seven membered ring containing one to three heteroatoms, optionally and independently substituted with one or more of halogen, $C_{1-12}$ alkyl, $C_{1-12}$ alkenyl, $C_{2-12}$ alkynyl, $C_{1-12}$ haloalkyl, $C_{3-12}$ carbocyclyl, $C_{3-12}$ heterocyclyl, $OR^5$, $SR^5$, $NO_2$, CN, $NR^5{}_2$, $NR^5COR^5$, $NR^5CONR^5{}_2$, $NR^5COR^5$, $NR^5CO_2R^5$, $CO_2R^5$, $COR^5$, $CONR^5{}_2$, $S(O)_2R^5$, $SONR^5{}_2$, $S(O)R^5$, $SO_2NR^5{}_2$, or $NR^5S(O)_2R^5$; and each saturated carbon in the optional ring is further optionally and independently substituted by =O, =S, NNR$^6{}_2$, =N—OR$^6$, =NNR$^6$COR$^6$, =NNR$^6$CO$_2$R$^6$, =NNSO$_2$R$^6$, or =NR$^6$;

wherein $R^3$ is hydrogen, $C_{1-6}$ alkyl, $C_{1-6}$ haloalkyl, or $C_{6-12}$ aryl;

wherein $R^4$ is hydrogen, $C_{1-6}$ alkyl, $C_{1-6}$ haloalkyl or $C_{6-12}$ aryl;

wherein $R^5$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^7$, $SR^7$, $NO_2$, CN, $NR^7R^7$, $NR^7COR^7$, $NR^7CONR^7R^7$, $NR^7COR^7$, $NR^7CO_2R^7$, $CO_2R^7$, $COR^7$, $CONR^7{}_2$, $S(O)_2R^7$, $SONR^7{}_2$, $S(O)R^7$, $SO_2NR^7R^7$, $NR^7S(O)_2R^7$, wherein the $C_{1-12}$ alkyl group optionally incorporates one or two insertions selected from the group consisting of —O—, —N($R^7$)—, —S(O)— and —S(O$_2$)—, wherein each $R^7$ may be the same or different and is as defined below;

wherein $R^6$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^7$ $SR^7$, $NO_2$, CN, $NR^7R^7$, $NR^7COR^7$, $NR^7CONR^7R^7$, $NR^7COR^7$, $NR^7CO_2R^7$, $CO_2R^7$, $COR^7$, $CONR^7{}_2$, $S(O)_2R^7$, $S(O)R^7$, $SO_2NR^7R^7$, $NR^7S(O)_2R^7$, wherein the $C_{1-12}$ alkyl group optionally incorporates one or two insertions selected from the group consisting of —O—, —N($R^7$)—, —S(O)— and —S(O$_2$)—, wherein each $R^7$ may be the same or different and is as defined below;

wherein $R^7$ is hydrogen, $C_{1-6}$ alkyl, or $C_{1-6}$ haloalkyl;

wherein the optionally substituted carbocyclyl or heterocyclyl group in $R^1$ and Z is optionally and independently fused to a partially saturated, unsaturated or fully saturated five to seven membered ring containing zero to three heteroatoms, and each substitutable carbon atom in $R^1$ or Z, including the optional fused ring, is optionally and independently substituted by one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $(CH_2)_nOR^{12}$, $(CH_2)_nNR^{12}{}_2$, $OR^{12}$, $SR^{12}$, $NO_2$, CN, $NR^{12}{}_2$, $NR^{12}COR^{12}$, $NR^{12}CONR^{12}{}_2$, $NR^{12}COR^{12}$, $NR^{12}CO_2R^{12}$, $CO_2R^{12}$, $COR^{12}$, $CONR^{12}{}_2$, $S(O)_2R^{12}$, $SONR^{12}{}_2$, $S(O)R^{12}$, $SO_2NR^{12}{}_2$, or $NR^{12}S(O)_2R^{12}$ wherein the $C_{1-12}$ alkyl group optionally contains one or more insertions selected from —O—, —N($R^{12}$)— —S—, —S(O)— and —S(O$_2$)—; and each saturated carbon in the optional fused ring is further optionally and independently substituted by =O, =S, NNR$^{13}{}_2$, =N—OR$^{13}$, =NNR$^{13}$COR$^{13}$, =NNR$^{13}$CO$_2$R$^{13}$, =NNSO$_2$R$^{13}$, or =NR$^{13}$; and each substitutable nitrogen atom in $R^1$ is optionally substituted by $R^{14}$, $COR^{14}$, $SO_2R^{14}$ or $CO_2R^{14}$;

wherein n is 1 to 6, preferably n is 1, 2 or 3;

wherein $R^{12}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{15}$, $SR^{15}$, $NO_2$, CN, $NR^{15}R^{15}$, $NR^{15}COR^{15}$, $NR^{15}CONR^{15}R^{15}$, $NR^{15}COR^{15}$, $NR^{15}CO_2R^{15}$, $CO_2R^{15}$, $COR^{15}$, $CONR^{15}{}_2$, $S(O)_2R^{15}$, $SONR^{15}{}_2$, $S(O)R^{15}$, $SO_2NR^{15}R^{15}$, $NR^{15}S(O)_2R^{15}$, wherein the $C_{1-12}$ alkyl group optionally incorporates one or two insertions selected from the group consisting of —O—, —N($R^{15}$)—, —S(O)— and —S(O$_2$)—, wherein each $R^{15}$ may be the same or different and is as defined below;

wherein two $R^{12}$ in $NR^{12}{}_2$ may form a partially saturated, unsaturated or fully saturated five to seven membered ring containing one to three heteroatoms, optionally and independently substituted with one or more of halogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $OR^{16}$, $SR^{16}$, $NO_2$, CN, $NR^{16}{}_2$, $NR^{16}COR^{16}$, $NR^{16}CONR^{16}{}_2$, $NR^{16}COR^{16}$, $NR^{16}CO_2R^{16}$, $CO_2R^{16}$, $COR^{16}$, $CONR^{16}{}_2$, $S(O)_2R^{16}$, $SONR^{16}{}_2$, $S(O)R^{16}$, $SO_2NR^{16}{}_2$, or $NR^{16}S(O)_2R^{16}$; and each saturated carbon in the optional ring is further optionally and independently substituted by =O, =S, NNR$^{17}{}_2$, =N—OR$^{17}$, =NNR$^{17}$COR$^{17}$, =NNR$^{17}$CO$_2$R$^{17}$, =NNSO$_2$R$^{17}$, or =NR$^{17}$;

wherein $R^{13}$ is hydrogen, $C_{1-12}$ alkyl, $C_{3-12}$ carbocyclyl or $C_{3-12}$ heterocyclyl, optionally substituted by one or more of $C_{1-6}$ alkyl, halogen, $C_{1-6}$ haloalkyl, $OR^{15}$ $SR^{15}$, $NO_2$, CN, $NR^{15}R^{15}$, $NR^{15}COR^{15}$, $NR^{15}CONR^{15}R^{15}$, $NR^{15}COR^{15}$, $NR^{15}CO_2R^{15}$, $CO_2R^{15}$, $COR^{15}$, $CONR^{15}{}_2$, $S(O)_2R^{15}$, $S(O)R^{15}$, $SO_2NR^{15}R^{15}$, $NR^{15}S(O)_2R^{15}$, wherein the $C_{1-12}$ alkyl group optionally incorporates one or two insertions selected from the group consisting of —O—, —N(R$^{15}$)—, —S (O)— and —S(O$_2$)—, wherein each R$^{15}$ may be the same or different and is as defined below;

wherein R$^{14}$ is hydrogen, C$_{1-6}$ alkyl, C$_{1-6}$ haloalkyl, or C$_{6-12}$ aryl;

wherein R$^{15}$ is hydrogen, C$_{1-6}$ alkyl, or C$_{1-6}$ haloalkyl;

wherein R$^{16}$ is hydrogen, C$_{1-12}$ alkyl, C$_{3-12}$ carbocyclyl or C$_{3-12}$ heterocyclyl, optionally substituted by one or more of C$_{1-6}$ alkyl, halogen, C$_{1-6}$ haloalkyl, OR$^{18}$, SR$^{18}$, NO$_2$, CN, NR$^{18}$R$^{18}$, NR$^{18}$COR$^{18}$, NR$^{18}$CONR$^{18}$R$^{18}$, NR$^{18}$COR$^{18}$, NR$^{18}$CO$_2$R$^{18}$, CO$_2$R$^{18}$, COR$^{18}$, CONR$^{18}{}_2$, S(O)$_2$R$^{18}$, SONR$^{18}{}_2$, S(O)R$^{18}$, SO$_2$NR$^{18}$R$^{18}$, NR$^{18}$S(O)$_2$R$^{18}$, wherein the C$_{1-12}$ alkyl group optionally incorporates one or two insertions selected from the group consisting of —O—, —N(R$^{18}$)—, —S(O)— and —S(O$_2$)—, wherein each R$^{18}$ may be the same or different and is as defined below;

wherein R$^{17}$ is hydrogen, C$_{1-12}$ alkyl, C$_{3-12}$ carbocyclyl or C$_{3-12}$ heterocyclyl, optionally substituted by one or more of C$_{1-6}$ alkyl, halogen, C$_{1-6}$ haloalkyl, OR$^{18}$, SR$^{18}$, NO$_2$, CN, NR$^{18}$R$^{18}$, NR$^{18}$COR$^{18}$, NR$^{18}$CONR$^{18}$R$^{18}$, NR$^{18}$COR$^{18}$, NR$^{18}$CO$_2$R$^{18}$, CO$_2$R$^{18}$, COR$^{18}$, CONR$^{18}{}_2$, S(O)$_2$R$^{18}$, S(O)R$^{18}$, SO$_2$NR$^{18}$R$^{18}$, NR$^{18}$S(O)$_2$R$^{18}$, wherein the C$_{1-12}$ alkyl group optionally incorporates one or two insertions selected from the group consisting of —O—, —N(R$^{18}$)—, —S(O)— and —S(O$_2$)—, wherein each R$^{18}$ may be the same or different and is as defined below; and wherein R$^{18}$ is hydrogen, C$_{1-6}$ alkyl, or C$_{1-6}$ haloalkyl.

2. A compound as claimed in claim 1 wherein R$^1$ is preferably a five or six membered carbocyclyl or heterocyclyl group wherein the carbocyclyl or heterocyclyl group is optionally fused to one or more unsaturated rings and the carbocyclyl, heterocyclyl or fused rings can be optionally substituted.

3. A compound as claimed in claim 1 wherein R$^1$ is optionally substituted phenyl, cyclohexyl, acridine, benzimidazole, benzofuran, benzothiophene, benzoxazole, benzothiazole, furan, imidazole, indole, isoindole, isoquinoline, isoxazole, isothiazole, morpholine, napthaline, oxazole, phenazine, phenothiazine, phenoxazine, piperazine, piperidine, pyrazole, pyridazine, pyridine, pyrrole, quinoline, quinolizine, tetrahydrofuran, tetrazine, tetrazole, thiophene, thiazole, thiomorpholine, thianaphthalene, thiopyran, triazine, triazole, or trithiane.

4. A compound as claimed in claim 1, wherein R$^1$ is optionally substituted with one or more of OR$^{12}$, NR$^{12}{}_2$, SR$^{12}$, (CH$_2$)$_n$OR$^{12}$, (CH$_2$)$_n$NR$^{12}{}_2$, halogen, C$_{1-6}$ alkyl, C$_{2-6}$ alkenyl, C$_{2-6}$ alkynyl, haloalkyl, NO$_2$, CN, CO$_2$R$^{12}$, COR$^{12}$, CONR$^{12}{}_2$, S(O)$_2$R$^{12}$, S(O)R$^{12}$ or SO$_2$NR$^{12}{}_2$;

wherein R$^{12}$ is hydrogen, C$_{1-4}$ alkyl, heterocyclyl or aryl and n is 1, 2, 3, 4, 5 or 6, and each substitutable nitrogen atom in R$^1$ is optionally substituted by R$^{14}$, COR$^{14}$, SO$_2$R$^{14}$ or CO$_2$R$^{14}$;

wherein R$^{14}$ is C$_{1-6}$ alkyl, C$_{1-6}$ haloalkyl, or C$_{6-12}$ aryl.

5. A compound as claimed in claim 1 selected from

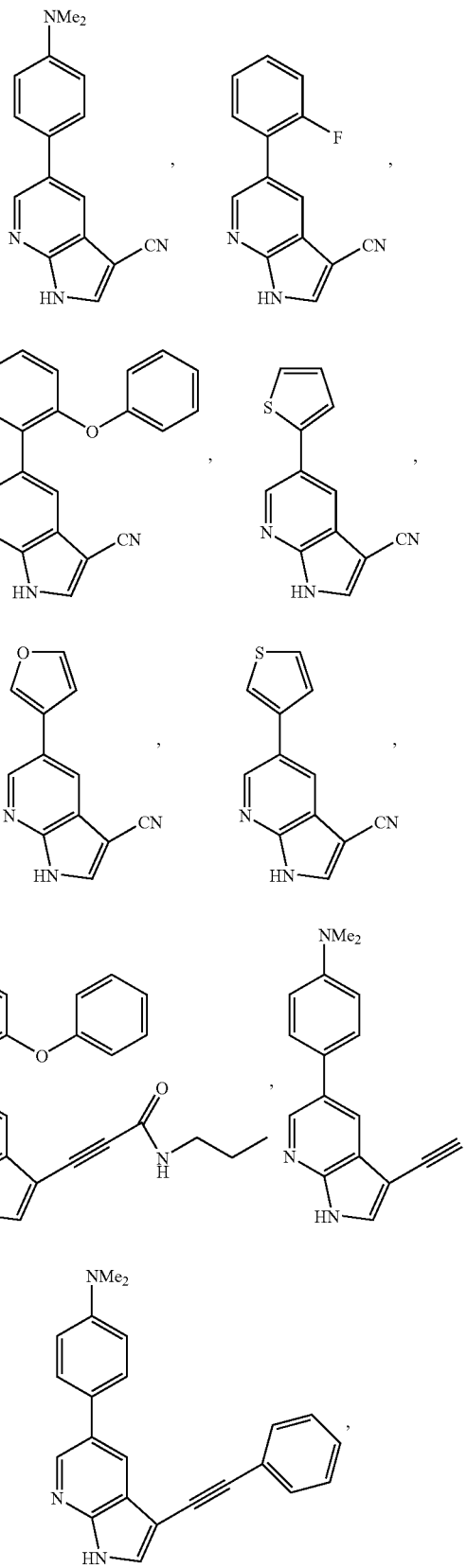

-continued

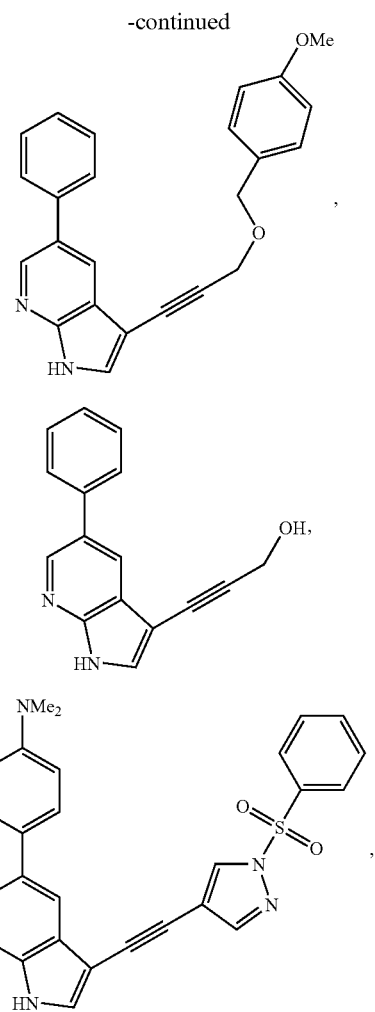

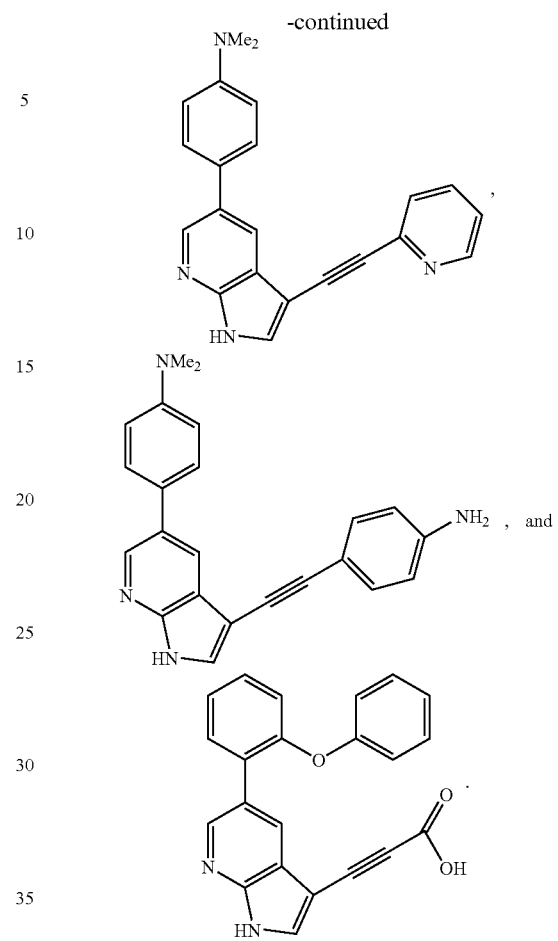

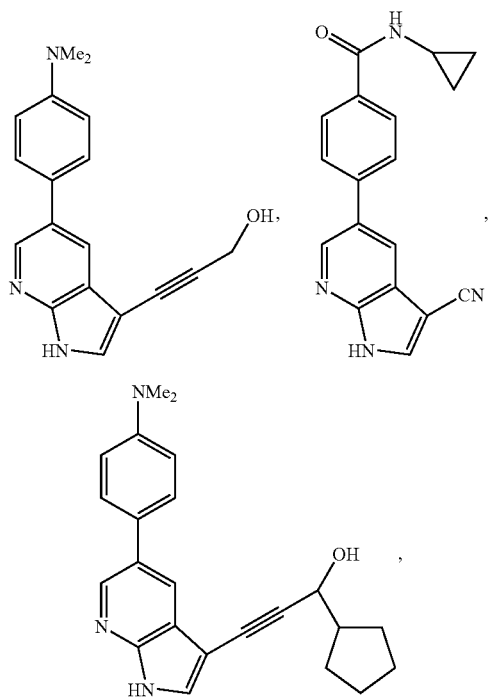

6. A process for the production of a compound of formula (I) as claimed in claim 1,

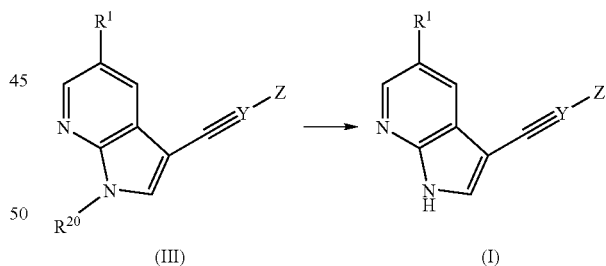

comprising the conversion of a compound of formula (III) to a compound of formula (I) by the removal of the group $R^{20}$;

wherein $R^1$ is as defined in claim 1 and $R^{20}$ is an amino protecting group.

7. A process as claimed in claim 6 wherein $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $(R^{30})SiOCH_2$, $(R^{30}O)_2CH$, $t\text{-BuOC(O)CH}_2$, $Me_2NCH_2$ or tetrahydropyranylamine, wherein $R^{30}$ is $C_{1-6}$ alkyl or $C_{6-12}$ aryl.

8. A process as claimed in claim 7 wherein $R^{20}$ is sulfonamide, and deprotection is carried out under basic conditions.

9. An intermediate of formula (III)

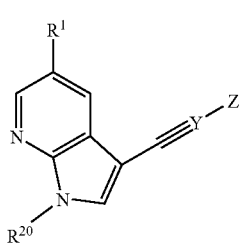

wherein $R^1$, Y and Z are is as defined in claim 1 and $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $(R^{30})SiOCH_2$, $(R^{30}O)_2CH$, $t\text{-}BuOC(O)CH_2$, $Me_2NCH_2$ or tetrahydropyranylamine, wherein $R^{30}$ is $C_{1-6}$ alkyl or $C_{6-12}$ aryl.

10. A process for the production of an intermediate of formula (III)

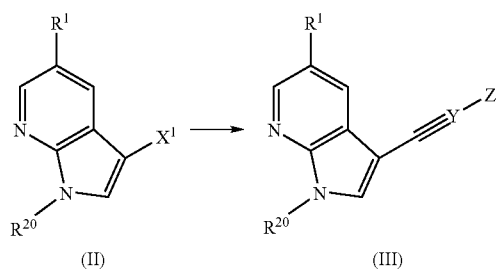

by the palladium catalyzed introduction of the group C≡Y-Z into compound (II), wherein $R^1$, Y and Z are as defined in claim 1, $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $R^{30}CH_2CH_2$, $R^{30}CH_2$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $R^{30})SiOCH_2$, $(R^{30}O)_2CH$, $t\text{-}BuOC(O)CH_2$, $Me_2NCH_2$ or tetrahydropyranylamine, wherein $R^{30}$ is $C_{1-6}$ alkyl or $C_{6-12}$ aryl and $X^1$ is F, Cl, Br I or $CF_3SO_3$.

11. A process as claimed in claim 10

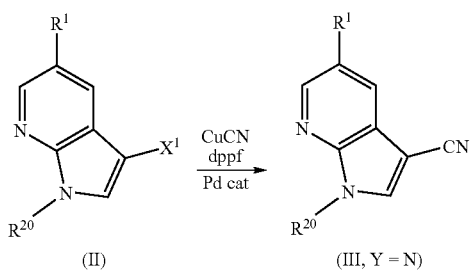

wherein the compound of formula III, (Y=N) is produced from a compound of formula (II) by incubation with a CuCN, 1,1'-bis(diphenylphosphino)ferrocene (dppf) and a palladium catalyst wherein $R^1$, $R^{20}$ and $X^1$ are as defined in claim 10.

12. A process as claimed in claim 10

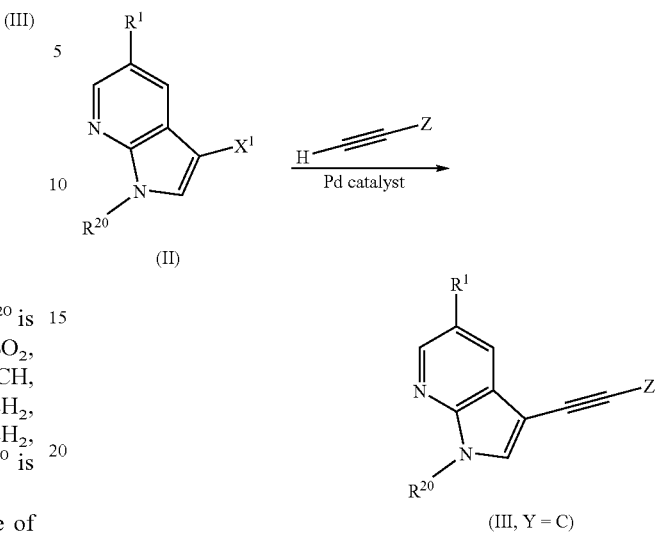

wherein the compound of formula III, (Y=C) is produced from a compound of formula (II) by incubation with an acetylene derivative H—C≡C-Z, a palladium catalyst and CuI, wherein $R^1$, $R^{20}$, $X^1$ and Z are as defined in claim 10.

13. A process for the production of an intermediate of formula (III)

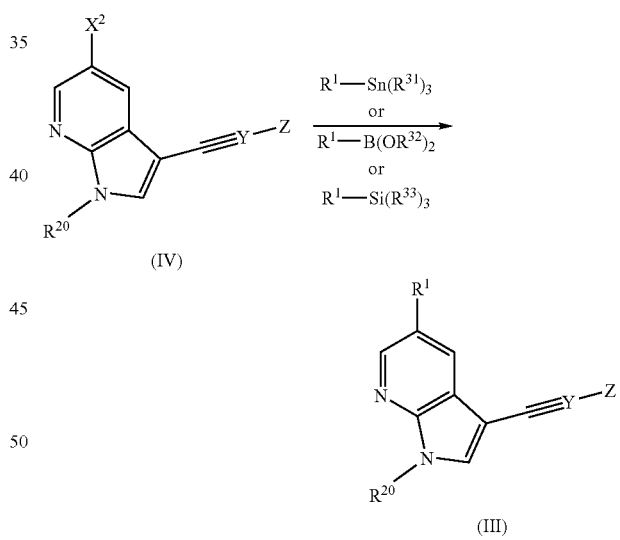

comprising a a) reaction of a compound of formula (IV) with stannane $R^1$—$Sn(R^{31})_3$ in the presence of a palladium catalyst or
b) reaction of a compound of formula (IV) with boronic acid or ester $R^1$—$B(OR^{32})_2$ in a presence of a suitable palladium catalyst or
c) reaction of a compound of formula (IV) with silane $R^1$—$Si(R^{33})_3$ in the presence of a palladium catalyst;
wherein $R^1$, Y and Z are as defined in claim 1, $X^2$ is a halide and $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, HO—$CH_2$, $R^{30}OCH_2$, $(R^{30})SiOCH_2$, $(R^{30}O)_2CH$, t-BuOC(O)$CH_2$, $Me_2NCH_2$ or tetrahydropyranylamine, wherein $R^{30}$ is $C_{1-6}$ alkyl or $C_{6-12}$ aryl;

wherein each of $R^{31}$ is independently $C_{1-6}$ alkyl, wherein each of $R^{32}$ is independently hydrogen or $C_{1-6}$ alkyl or wherein two $R^{32}$ groups together form a five, six or seven membered optionally ring with the boron and oxygen atoms, wherein the ring is optionally substituted with one or more $C_{1-6}$ alkyl group, and wherein $R^{33}$ is independently $C_{1-6}$ alkyl, F, OH.

14. A process as claimed in claim 13 wherein $R^{32}$ is hydrogen or both $R^{32}$ groups form the group —C($CH_3$)$_2$—C(CH3)$_2$—.

15. A process as claimed in claim 13 wherein the palladium catalyst is $(PPh_3)_2PdCl_2$, $(PPh_3)_4Pd$, $Pd(OAc)_2$, $[PdCl(\eta^3\text{-}C_3H_5]_2$, $Pd_2(dba)_3$(wherein dba=dibenzylidenacetone) or Pd/P(t-Bu)$_3$.

16. A process for the production of a compound of formula (I) as defined in claim 1,

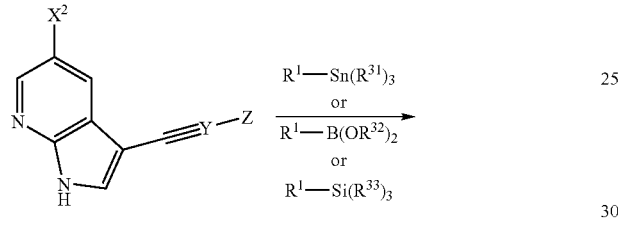

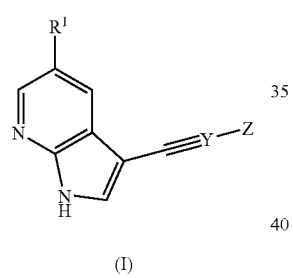

(I)

comprising a a) reaction of a compound of formula (V) with stannane $R^1$—Sn($R^{31}$)$_3$ in the presence of a palladium catalyst; or b) reaction of a compound of formula (V) with boronic acid or ester $R^1$—B($OR^{32}$)$_2$ in a presence of a suitable palladium catalysts; or c) reaction of a compound of formula (V) with silane $R^1$—Si($R^{33}$)$_3$ in the presence of a palladium catalyst, wherein, $X^2$ is a halide, wherein each of $R^{31}$ is independently $C_{1-6}$ alkyl, wherein each of $R^{32}$ is independently hydrogen or $C_{1-6}$ alkyl or wherein two $R^{32}$ groups together form a five, six or seven membered optionally ring with the boron and oxygen atoms, wherein the ring is optionally substituted with one or more $C_{1-6}$ alkyl group, and wherein $R^{33}$ is independently $C_{1-6}$ alkyl, F, OH; and wherein $R^1$, Y and Z are as defined in claim 1.

17. A process as claimed in claim 16 wherein the palladium catalyst is $(PPh_3)_2PdCl_2$, $(PPh_3)_4Pd$, $Pd(OAc)_2$, $[PdCl(\eta^3\text{-}C_3H_5]_2$, $Pd_2(dba)_3$ (wherein dba=dibenzylidenacetone), or Pd/P(t-Bu)$_3$.

18. An intermediate of formula (V)

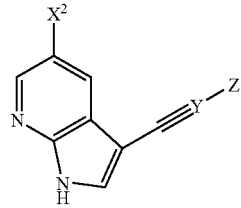

wherein Y and Z are as defined in claim 1, and wherein $X^2$ is a halide.

19. An intermediate of formula (V) as claimed in claim 18 wherein said compound is

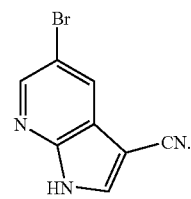

20. A process for the production of an intermediate of formula (V)

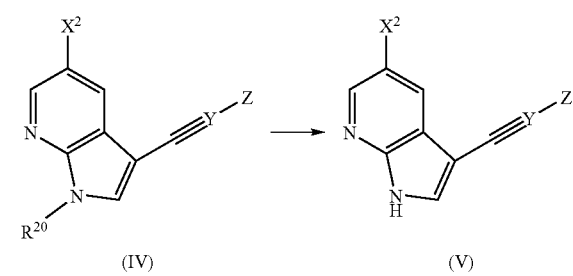

comprising the conversion of a compound of formula (IV) into a compound of formula (V) by removal of the group $R^{20}$, wherein Y and Z are as defined in claim 1, $X^2$ is a halide and $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30})CH$, PhC(O)$CH_2$, $CH_2$=CH, $ClCH_2CH_2$, $Ph_3C$, $Ph_2$(4-pyridyl)C, $Me_2N$, HO—$CH_2$, $R^{30}OCH_2$, $(R^{30}SiOCH_2$, $(R^{30}O)_2CH$, t-BuOC(O)$CH_2$, $Me_2NCH_2$ or tetrahydropyranylamine, wherein $R^{30}$ is $C_{1-6}$ alkyl or $C_{6-12}$ aryl.

21. An intermediate of formula (IV)

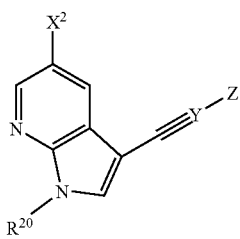

(IV)

wherein Y and Z are as defined in claim 1,
wherein $X^2$ is a halide and
wherein $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $(R^{30}SiOCH_2$, $(R^{30}O)_2CH$, t-BuOC(O)CH_2$, $Me_2NCH_2$ or tetrahydropyranylamine, wherein $R^{30}$ is $C_{1-6}$ alkyl or $C_{6-12}$ aryl.

22. A process for the production of an intermediate of formula (VII)

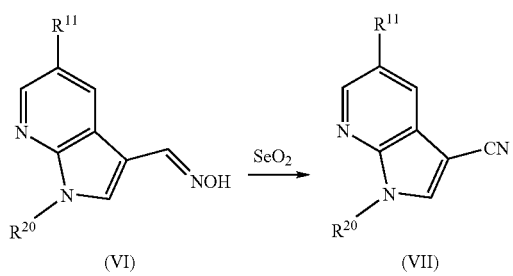

(VI) → (VII)

comprising the reaction of aldoxime (VI) with selenium dioxide,
wherein $R^{11}$ is $X^2$ or $R^1$;
wherein $X^2$ is a halide and $R^1$ is defined in claim 1;
and wherein $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $(R^{30}SiOCH_2$, $(R^{30}O)_2CH$, t-BuOC(O)CH_2$, $Me_2NCH_2$ or tetrahydropyranylamine, wherein $R^{30}$ is $C_{1-6}$ alkyl or $C_{6-12}$ aryl.

23. An intermediate of formula (VI)

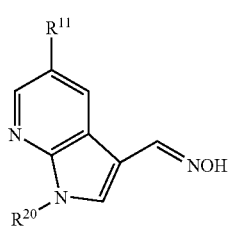

(VI)

wherein $R^{11}$ is as defined in claim 22, and $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{30}OCH_2$, $(R^{30}SiOCH_2$, $(R^{30}O)_2CH$, t-BuOC(O)CH_2$, $Me_2NCH_2$ or tetrahydropyranylamine, wherein $R^{30}$ is $C_{1-6}$ alkyl or $C_{6-12}$ aryl.

24. A process for the production of an intermediate of formula (VI)

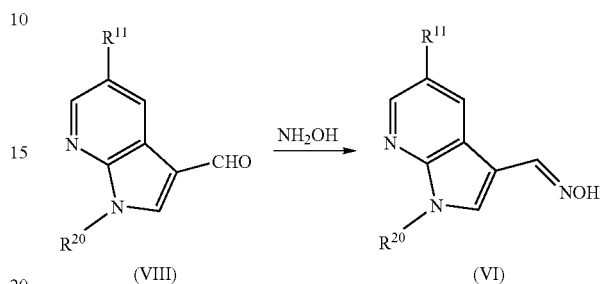

(VIII) → (VI)

comprising the reaction of aldehyde (VIII) with hydroxylamine,
wherein $R^{11}$ and $R^{20}$ are as defined in claim 22.

25. An intermediate of formula (VIII)

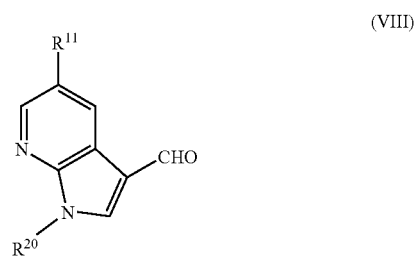

(VIII)

wherein $R^{11}$ and $R^{20}$ are as defined in claim 22.

26. A process for the production of an intermediate formula (VIII)

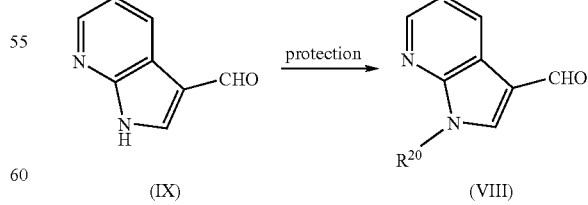

(IX) → (VIII)

comprising the addition of the $R^{20}$ group to a compound of general formula (IX) wherein $R^{11}$ and $R^{20}$ are as defined in claim 22.

27. An intermediate of formula (IX)

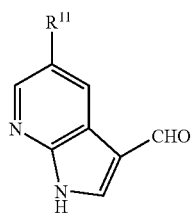

wherein $R^{11}$ is as defined in claim 22.

28. A process for the production of an intermediate of formula (IX)

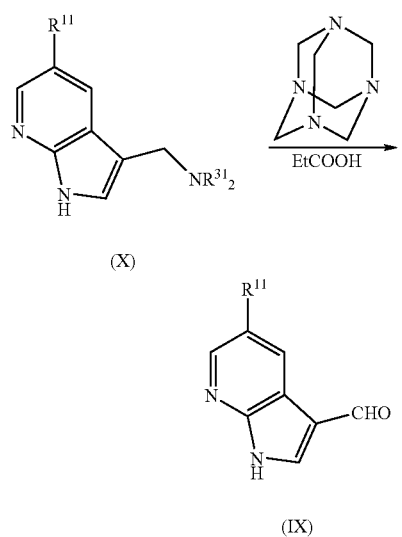

comprising the reaction of a compound of a formula (X) with hexamethylenetetramine in aqueous propionic acid wherein $R^{11}$ is as defined in claim 22, and $R^{31}$ is each independently $C_{1-6}$ alkyl.

29. A process for the production of an intermediate of formula (IV)

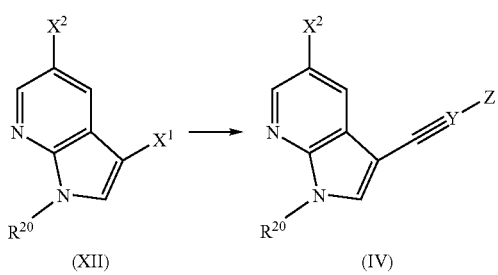

by the palladium catalyzed introduction of the group C≡Y-Z into compound (XII), wherein Y is N or C and Z is lone electron pair, hydrogen, $C_{1-12}$ alkyl, $C_{2-12}$ alkenyl, $C_{2-12}$ alkynyl, $C_{1-12}$ haloalkyl, $C_{3-12}$ carbocyclyl, $C_{3-12}$ heterocyclyl, $(CH_2)_nOR^2$, $(CH_2)_nNR^2_2$, $CO_2R^2$, $COR^2$, $CONR^2_2$, wherein the $C_{1-12}$ alkyl group optionally contains one or more insertions selected from —O—, —N($R^2$)— —S—, —S(O)— and —S($O_2$)—; and each substitutable nitrogen atom in Z is optionally substituted by $R^3$, $COR^3$, $SO_2R^3$ or $CO_2R^3$, $R^{20}$ is $R^{30}SO_2$, $R^{30}C(O)$, $(R^{30})_3Si$, $R^{30}OCH_2$, $(R^{30})_2NSO_2$, $R^{30}OC(O)$, $R^{30}(R^{30}O)CH$, $PhC(O)CH_2$, $CH_2$=CH, $ClCH_2CH_2$, $Ph_3C$, $Ph_2$(4-pyridyl)C, $Me_2N$, HO—$CH_2$, $R^{30}OCH_2$, $(R^{30})SiOCH_2$, $(R^{30}O)_2CH$, t-BuOC(O)$CH_2$, $Me_2NCH_2$ or tetrahydropyranylamine, wherein $R^{30}$ is $C_{1-6}$ alkyl or $C_{6-12}$ aryl, $X^1$ is F, Cl, Br I or $CF_3SO_3$ and $X^2$ is a halide.

30. A process as claimed in claim 29

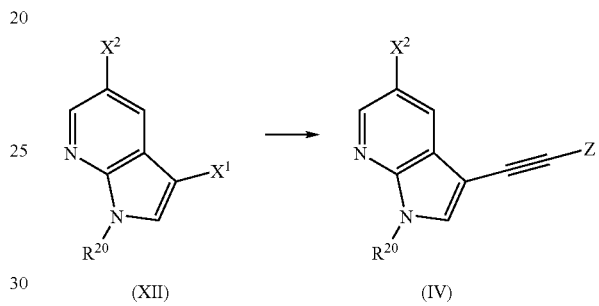

wherein the compound of formula (IV, Y=C) is produced from a compound of formula (XII) by incubation with an acetylene derivative H—C≡C-Z, a palladium catalyst and CuI;

wherein Y is C and Z, $R^{20}$, $X^1$ and $X^2$ are as defined in claim 29.

31. An intermediate selected from

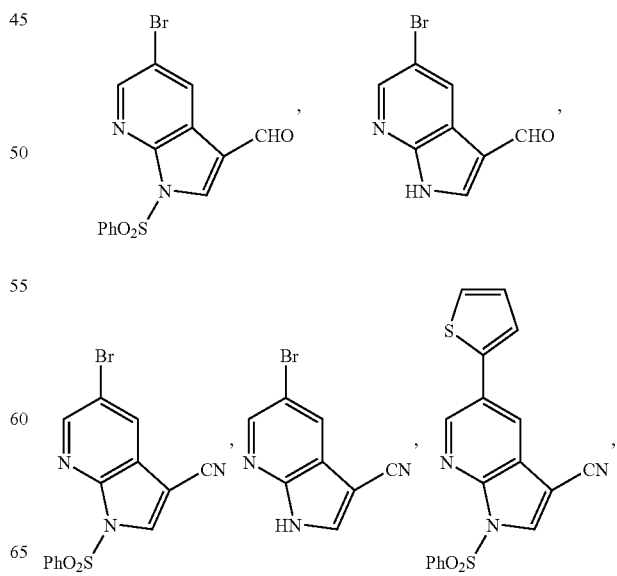

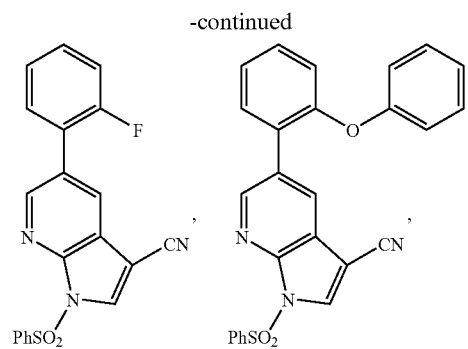
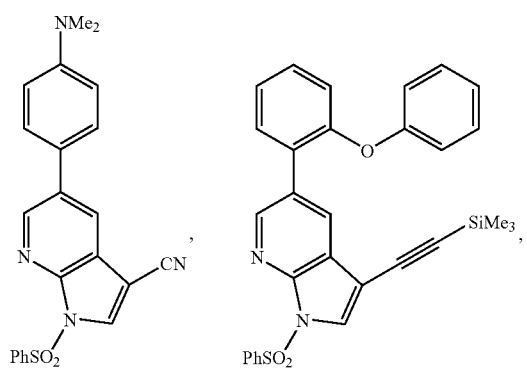
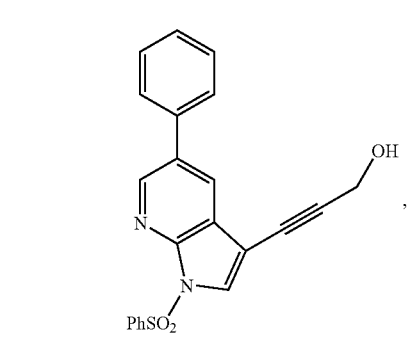
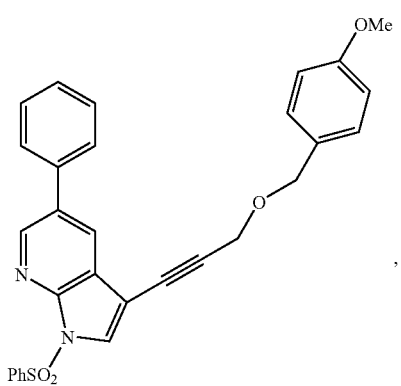
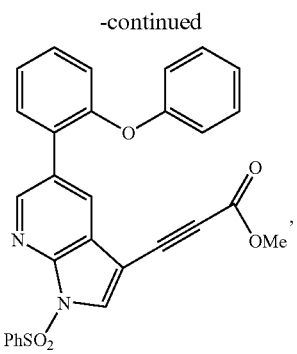
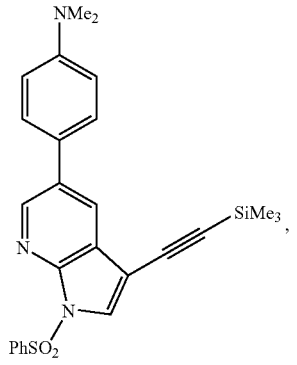
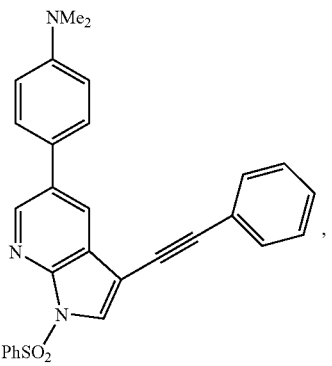
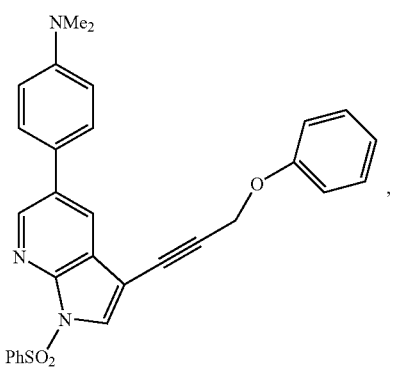

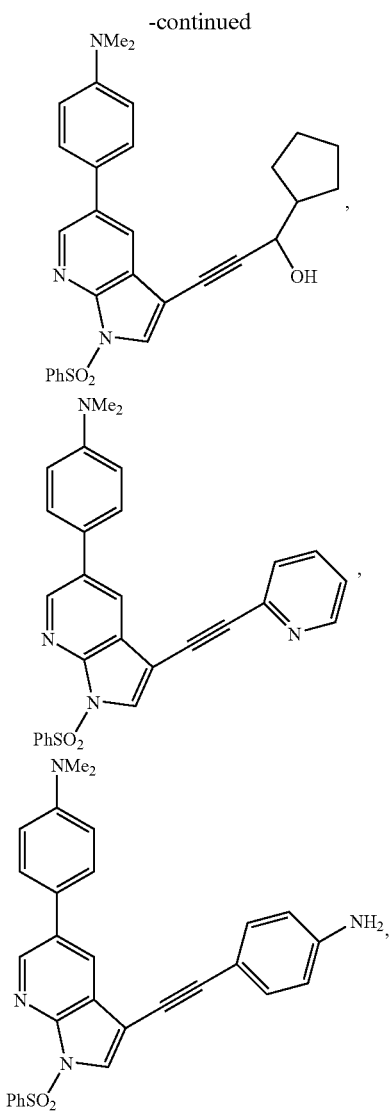

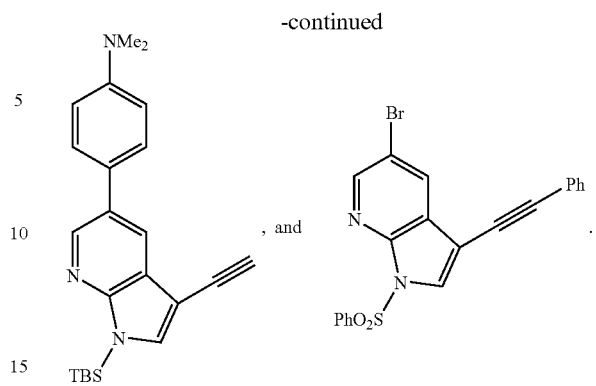

32. A pharmaceutical composition comprising a compound according to claim 1 in combination with a pharmaceutically acceptable carrier, diluent or excipient.

33. A composition as claimed in claim 32 further comprising one or more other active agent.

34. A composition as claimed in claim 33 wherein the composition further comprises an anti-inflammatory agent and/or an AMPA receptor antagonist.

35. A method of treating a JNK-mediated disorder in an individual, which method comprises administering to said individual a compound as claimed in claim 1.

36. A method as claimed in claim 35, wherein the disorder is an inflammatory disease and/or autoimmune disease such as Rheumatoid arthritis.

37. A method as claimed in claim 35, wherein the disorder is inflammatory bowel disorder or rheumatoid arthritis.

38. A method as claimed in claim 35, wherein one or more other active agent is administered to the individual simultaneously, subsequently or sequentially to administering the compound.

39. A method as claimed in claim 38, wherein the other active agent is an anti-inflammatory agent.

* * * * *

UNITED STATES PATENT AND TRADEMARK OFFICE
CERTIFICATE OF CORRECTION

| | | |
|---|---|---|
| PATENT NO. | : 7,612,086 B2 | Page 1 of 1 |
| APPLICATION NO. | : 10/554808 | |
| DATED | : November 3, 2009 | |
| INVENTOR(S) | : Graczyk et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 576 days.

Signed and Sealed this
Seventh Day of June, 2011

David J. Kappos
*Director of the United States Patent and Trademark Office*